United States Patent
Rahman et al.

(10) Patent No.: US 8,620,132 B2
(45) Date of Patent: Dec. 31, 2013

(54) TERAHERTZ SCANNING REFLECTOMETER

(76) Inventors: Anis Rahman, Hummelstown, PA (US); Aunik K. Rahman, Hummelstown, PA (US)

( * ) Notice: Subject to any disclaimer, the term of this patent is extended or adjusted under 35 U.S.C. 154(b) by 112 days.

(21) Appl. No.: 13/423,032

(22) Filed: Mar. 16, 2012

(65) Prior Publication Data
US 2012/0228507 A1 Sep. 13, 2012

Related U.S. Application Data

(60) Continuation-in-part of application No. 13/281,230, filed on Oct. 25, 2011, now abandoned, and a division of application No. 11/862,474, filed on Sep. 27, 2007, now Pat. No. 8,050,531, application No. 13/423,032, which is a continuation-in-part of application No. 12/322,662, filed on Feb. 5, 2009, now abandoned, which is a continuation-in-part of application No. 11/862,473, filed on Sep. 27, 2007, now Pat. No. 7,919,755, and a continuation-in-part of application No. 11/862,474, filed on Sep. 27, 2007, now Pat. No. 8,050,531.

(60) Provisional application No. 61/454,157, filed on Mar. 18, 2011, provisional application No. 60/827,206, filed on Sep. 27, 2006, provisional application No. 61/026,233, filed on Feb. 5, 2008.

(51) Int. Cl.
*G01J 5/02* (2006.01)
*G02F 1/35* (2006.01)
*G02B 6/00* (2006.01)
*G02F 2/02* (2006.01)

(52) U.S. Cl.
USPC ...... 385/147; 359/326; 250/341.1; 250/341.8

(58) Field of Classification Search
USPC .............. 385/147; 359/326; 250/341.1, 341.8
See application file for complete search history.

(56) References Cited

U.S. PATENT DOCUMENTS

| | | | |
|---|---|---|---|
| 6,605,808 B2 * | 8/2003 | Mickan et al. | 250/341.8 |
| 6,865,014 B2 * | 3/2005 | Ciesla et al. | 359/326 |
| 6,957,099 B1 * | 10/2005 | Arnone et al. | 600/473 |
| 7,119,339 B2 * | 10/2006 | Ferguson et al. | 250/358.1 |
| 7,145,148 B2 * | 12/2006 | Alfano et al. | 250/341.8 |
| 7,214,940 B2 * | 5/2007 | Cluff et al. | 250/341.1 |
| 7,335,883 B2 * | 2/2008 | Wallace et al. | 250/330 |
| 7,368,280 B2 * | 5/2008 | Zhang et al. | 435/287.2 |
| 7,612,341 B2 * | 11/2009 | Fitzgerald et al. | 250/341.1 |
| 7,675,036 B2 * | 3/2010 | Taday et al. | 250/341.1 |
| 7,710,561 B2 * | 5/2010 | Roth | 356/302 |
| 7,728,296 B2 * | 6/2010 | Cole et al. | 250/338.1 |
| 8,050,531 B2 * | 11/2011 | Rahman et al. | 385/142 |
| 2002/0074500 A1 * | 6/2002 | Mickan et al. | 250/341.8 |
| 2004/0065832 A1 * | 4/2004 | Cluff et al. | 250/341.1 |
| 2004/0155193 A1 * | 8/2004 | Tran et al. | 250/341.1 |
| 2005/0023470 A1 * | 2/2005 | Ferguson et al. | 250/358.1 |
| 2005/0082479 A1 * | 4/2005 | Wallace et al. | 250/330 |
| 2005/0098728 A1 * | 5/2005 | Alfano et al. | 250/341.8 |

(Continued)

Primary Examiner — Rhonda Peace
(74) Attorney, Agent, or Firm — Dentons US LLP

(57) ABSTRACT

A terahertz scanning reflectometer is described herein. A high sensitivity terahertz scanning reflectometer is used to measure dynamic surface deformation and delamination characteristics in real-time. A number of crucial parameters can be extracted from the reflectance measurements such as dynamic deformation, propagation velocity, and final relaxation position. A terahertz reflectometer and spectrometer are used to determine the permeation kinetics and concentration profile of active ingredients in stratum corneum.

16 Claims, 18 Drawing Sheets

(56) References Cited

U.S. PATENT DOCUMENTS

| | | |
|---|---|---|
| 2006/0043298 A1* | 3/2006 | Kawase et al. ........... 250/339.06 |
| 2006/0231762 A1* | 10/2006 | Ohtake et al. .............. 250/341.8 |
| 2006/0255277 A1* | 11/2006 | Cole et al. .................. 250/341.1 |
| 2007/0257216 A1* | 11/2007 | Withers et al. ................ 250/580 |
| 2007/0296957 A1* | 12/2007 | Fitzgerald et al. .............. 356/51 |
| 2008/0006767 A1* | 1/2008 | Taday et al. ................. 250/252.1 |
| 2008/0017813 A1* | 1/2008 | Vetrovec et al. ........... 250/504 R |
| 2009/0206263 A1* | 8/2009 | Rahman ..................... 250/341.1 |
| 2009/0290149 A1* | 11/2009 | Roth .............................. 356/300 |
| 2009/0314944 A1* | 12/2009 | Evans et al. ................. 250/341.8 |
| 2012/0228507 A1* | 9/2012 | Rahman et al. .......... 250/339.11 |

* cited by examiner

S   Max. deformation
Δt  Time to max. deformation
$L_\tau$  Final relaxed position
τ   Relaxation time
$V_{max}$  Deformation velocity

TERAHERTZ SCANNING REFLECTOMETER

CROSS REFERENCE TO RELATED APPLICATION

This application claims the benefit of U.S. Provisional Application No. 61/454,157, filed Mar. 18, 2011, the contents of which are hereby incorporated by reference herein and is a continuation-in-part of U.S. patent application Ser. No. 13/281,230, filed Oct. 25, 2011, which is a divisional of U.S. patent application Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof," filed Sep. 27, 2006; and a continuation-in-part of U.S. patent application Ser. No. 12/322,662, filed Feb. 5, 2009, which claims the benefit of U.S. Provisional Application No. 61/026,233, filed Feb. 5, 2008, entitled "Terahertz Time Domain and Frequency Domain Spectroscopy" and is a continuation-in-part of U.S. patent application Ser. No. 11/862,473, filed Sep. 27, 2007, which issued as U.S. Pat. No. 7,919,755 on Apr. 5, 2011, entitled "Dendrimer Based Electro-optic Sensor", and U.S. patent application Ser. No. 11/862,474, filed Sep. 27, 2007, which issued as U.S. Pat. No. 8,050,531 on Nov. 1, 2011, entitled "Dendrimer Based Terahertz Generator", all of which are herein incorporated in their entireties. This application is related to U.S. patent application Ser. No. 11/862,473, entitled "Dendrimer Based Electro-Optic Sensor", filed on Sep. 27, 2007, which issued as U.S. Pat. No. 7,919,755 on Apr. 5, 2011; U.S. patent application Ser. No. 10/710,303, filed Jul. 1, 2004, which issued as U.S. Pat. No. 7,389,029 on Jun. 17, 2008; U.S. patent application Ser. No. 11/335,110, filed on Jan. 19, 2006, which issued as U.S. Pat. No. 7,412,121 on Aug. 12, 2008; and U.S. patent application Ser. No. 10/605,638, filed on Oct. 15, 2003, which issued as U.S. Pat. No. 7,110,627 on Sep. 19, 2006, all of which are herein incorporated by reference.

FIELD OF INVENTION

This application is related to terahertz spectrometry and reflectometry.

BACKGROUND

The recently accessible terahertz (THz) portion of the electromagnetic spectra, also known as T-ray spectra, has a wide potential to be employed in materials, medical, biomedical, and biological studies and characterization.

Ballistic characterization of improved materials for Soldier personal protective equipment is an ever challenging task, requiring precise measurement of materials during ballistic impact. Current dynamic deformation technologies, such as high speed digital image correlation (DIC), and laser velocimetry and vibrometry, are only able to provide surface measurements. However, there is a need to measure the dynamic delamination and mass loss of composite material, allowing calculation of available kinetic energy contributing to the trauma in non-lethal cases. Further, characterization of diffusion kinetics and depth profiling of permeating analytes is also important for basic studies of transdermal drug delivery and diagnostics.

Terahertz spectrometry is an emerging novel technique that has great potential in diagnosis of certain disease conditions as well as in the analysis of actives in certain biological tissues. Broadband terahertz technology utilizes frequencies from ~100 GHz to over 30 THz that can be used to obtain tomographic information on the tissue surface and its interior, as well as interaction of the actives with tissue.

SUMMARY

A terahertz scanning reflectometer is described herein. A high sensitivity terahertz scanning reflectometer is used to measure dynamic surface deformation and delamination characteristics in real-time. A number of crucial parameters can be extracted from the reflectance measurements such as dynamic deformation, propagation velocity, and final relaxation position. A terahertz reflectometer and spectrometer are used to determine the permeation kinetics and concentration profile of active ingredients in stratum corneum.

BRIEF DESCRIPTION OF THE DRAWINGS

A more detailed understanding may be had from the following description, given by way of example in conjunction with the accompanying drawings wherein.

DETAILED DESCRIPTION

Engineering of improved materials for soldier personal protective equipment is an ever challenging task involving characterization of relevant materials to help develop better helmet and body armor performance against ballistic and blunt impact threats. However, the current technologies face limitations in arriving at precise information regarding ballistic impact events that are crucial for effective characterization. A high sensitivity terahertz scanning reflectometer (TSR) is used to measure the dynamic surface deformation characteristics in real-time (in-situ) and also at post deformation (ex-situ).

Real-time measurements can capture the kinetics of deformation of layered materials due to ballistic impact. Since terahertz radiation can penetrate many composite materials, a clearer picture is produced of the internal layers of composite laminates than is otherwise possible. A number of crucial parameters can be extracted from the kinetics measurement, such as the deformation length, the propagation velocity, and the final relaxation position, including any vibrational motions due to impact. In addition, for non-metallic substrates, a transmitted beam may be used to calibrate any mass loss of the laminate layers due to impact. This will allow computation of the force and energy of impact in real-time.

The current technologies have limitations in that they are not sensitive to certain important parameters, such as kinetics and dynamic mass loss that are crucial to fully quantify a ballistic event. Terahertz radiation interaction with materials provides much higher sensitivity because the probing frequencies are sensitive to vibration of molecules as a whole as opposed to just a bond or its torsion.

FIG. 1(a) illustrates a terahertz scanning reflectometer capturing ballistic kinetics of a target. A terahertz scanning reflectometer (TSR) 100 in a horizontal orientation with respect to a target 110. A sketch of the transient (kinetics) of deformation depth and recovery profile is shown in FIG. 1(b) and a 1D scan across the deformation is shown in FIG. 1(c).

The TSR design is based on normal incidence of the terahertz beam to the target. In case of normal incidence, the incident beam is the sum of the reflected, transmitted and absorbed intensities. Assuming the material properties remain unchanged during the impact, real-time measurement of reflectance represents the deformation at the point of impact. Ordinarily, the Beer-Lambert's law is used to determine the concentration dependence, C, of a solute in a solvent from absorbance data: $A=\epsilon lC$, where l is the path length and $\epsilon$ is the extinction coefficient (or molar absorptivity). However, for a ballistic impact, all material parameters may be assumed fixed, with the path length l becoming a function of time, l(t), due to deformation. Since the reflectance, R, is proportional to the variation in path length, measurement of R(t) can yield the dynamics of deformation.

Figure 1:
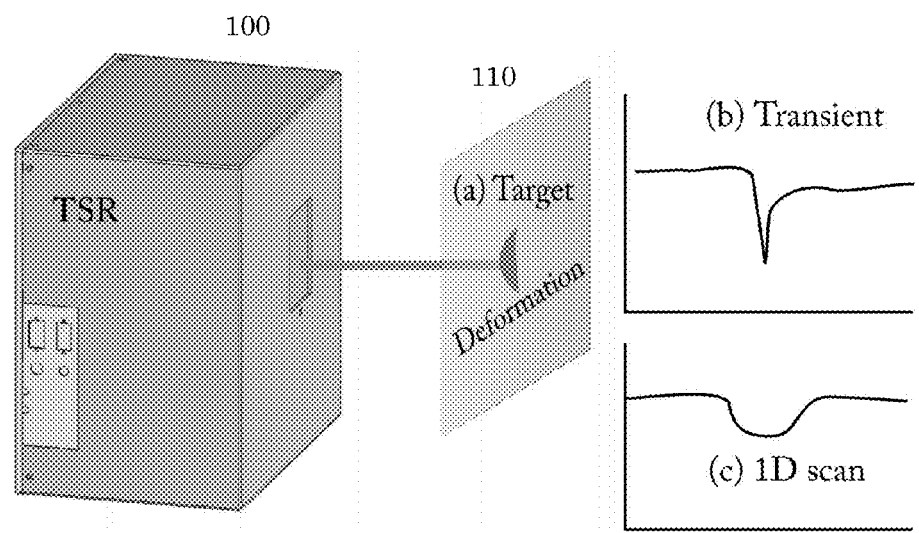
FIG. 1(a) shows an example of a terahertz scanning reflectometer in horizontal orientation; 1(b) shows a transient and 1(c) shows a 1D scan.

As illustrated in FIG. 1, when the terahertz beam reflected by the target (see FIG. 1(a)), the transient due to impact (see FIG. 1(b)) represents the nature of deformation at impact. However, a difficulty with the normal incidence configuration is that it is not the most suitable configuration for field testing of actual ballistic events; because, in case the projectile penetrates the target, it may damage the machine via direct impact in its path. Therefore, the architecture is required such that the transmitter and the detection unit may be mounted separately in an angular orientation such that the vulnerabilities for direct hit with a projectile may be avoided. This configuration is illustrated in FIG. 2.

Figure 2:
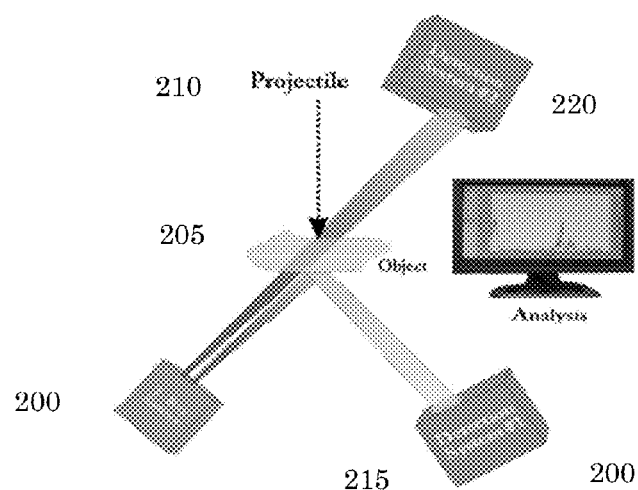
FIG. 2 is an example two-channel terahertz dynamic scanning reflectometer for real-time kinetics of ballistic events.

FIG. 2 shows a configuration having a terahertz ray source 200 that is aligned with an object 205 that is impacted by a projectile 210. A first detector system 215 is situated at an angle such that the projectile 210, if it passes through the object 205, passes between the terahertz ray source 200 and detection system 215. A second detection system 220 is situated linearly across from the terahertz ray source 200 for direct/transmission measurements. This arrangement captures both direct and reflected radiation from projectile 210 impacting object 205.

The TSR uses a continuous wave (CW) terahertz source that generates broadband terahertz radiation from an electro-optic dendrimer as disclosed, for example, in U.S. Ser. No. 13/281,230, filed Oct. 25, 2011, which is a divisional of U.S. Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof, filed Sep. 27, 2006; and a continuation-in-part of U.S. Ser. No. 12/322,662, filed Feb. 5, 2009, which claims the benefit of U.S. Provisional Application Ser. No. 61/026,233, filed Feb. 5, 2008 and entitled "Terahertz Time Domain and Frequency Domain Spectroscopy" and is a continuation-in-part of U.S. patent application Ser. No. 11/862,473, filed Sep. 27, 2007, and entitled "Dendrimer Based Electro-optic Sensor", which was published as U.S. 20080128618 on Jun. 5, 2008 and U.S. patent application Ser. No. 11/862,474, filed Sep. 27, 2007, and entitled "Dendrimer Based Terahertz Generator", which was published as U.S. Publication No. 2008/0099698 on May 1, 2008, all of which are herein incorporated in their entireties.

Figure 3:
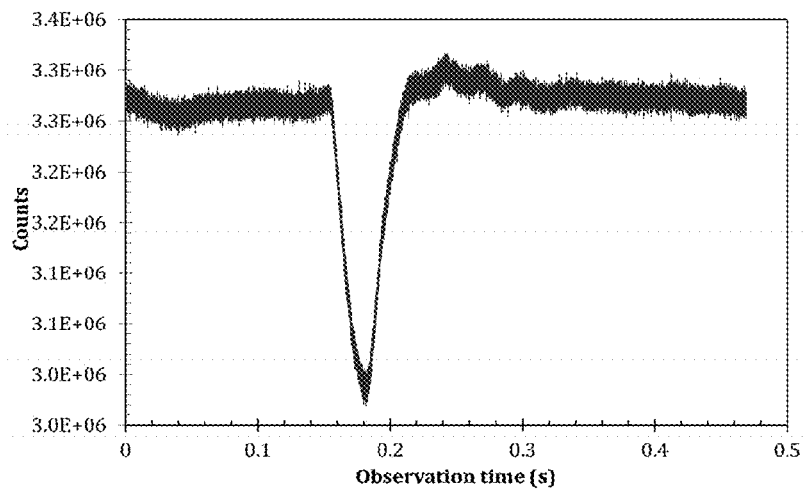
FIG. 3 shows deformation kinetics of the arrangement of FIG. 2.

FIG. 3 shows the kinetics of impact of a specimen 300 impacted by a pendulum 310. A terahertz beam is focused on the specimen 300 at normal incidence while a matching detection system 315 captures the reflected beam at a suitable distance. At this configuration a sudden impact results in a transient that is directly related to the deformation characteristics. The following parameters can be extracted from the kinetics spectra: Max deformation ($l_{max}$); Time to max deformation ($\Delta t$); Max relaxation ($\Delta l$ %); position of the final relaxed state ($l_r$) and the relaxation time, $\tau$; and deformation speed ($\upsilon$). These parameters will be used to uniquely characterize different candidate materials as well.

Another factor in the characterization scheme is the delamination of interior layers of a multilayered material. A feature of terahertz radiation is the ability to penetrate many materials including multilayer nonmetallic helmets and body armors. This facilitates inspection of delamination, inclusions, and impregnation by foreign particles. Additionally, the calibrated transmitted beam provides the change in mass at impact from which the impact force may be computed by combining with kinetics data.

Referring back to FIG. 3, the specimen is an acrylic plate that is struck with a blunt pendulum impactor and dynamic deformation is captured in real time. Reflectance kinetics is converted to deformation and the velocity was calculated from the kinetics spectrum. Kinetics of a focused pendulum impactor on a steel plate was also acquired, characterizing plate relaxation from maximum deformation to equilibrium with discernible vibrations before reaching stable equilibrium.

Deformation kinetics of an acrylic plate and a steel plate was measured. The acrylic plate was mounted on a mandible, struck with a pendulum and the ballistic kinetics was captured in real time as shown in FIG. 3. FIG. 3 shows that when a target is placed on the displacement curve, the measured power remains steady as long as the target remains fixed. A sudden displacement (deformation) of the target causes the power drop proportional to the displacement and then becomes steady at the new position. Therefore, the power measured in real-time generates a kinetics curve (inset) from which corresponding displacement can be quantified.

Figure 4:
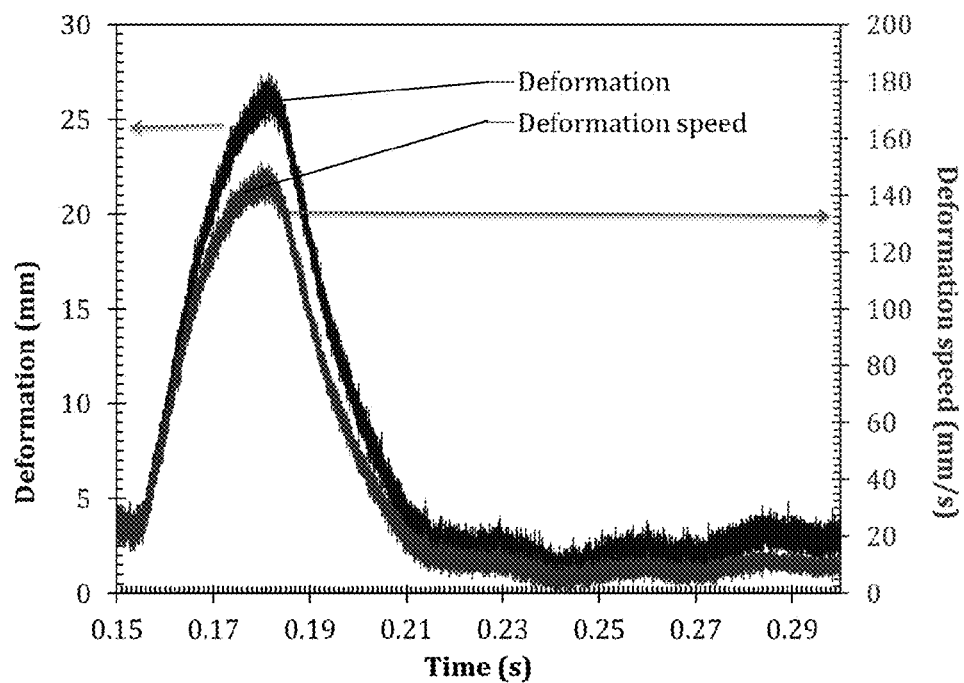
FIG. 4 shows acrylic deformation calculated from the kinetics data of FIG. 2 where the dark curve represents 27 mm (from DIC) over ~30 ms and propagation speed of deformation is shown by the light curve.

FIG. 4 shows the computed deformation where the reflectance kinetics was converted to a known deformation of 27 mm (from digital image correlation (DIC)) and the propagation speed calculated from the kinetics spectrum. The figure shows the instantaneous deformation and relaxation of a panel struck by a small hammer (by hand). Displacement corresponding to the change in reflected power read off of the calibration curve (inset).

Figure 5:
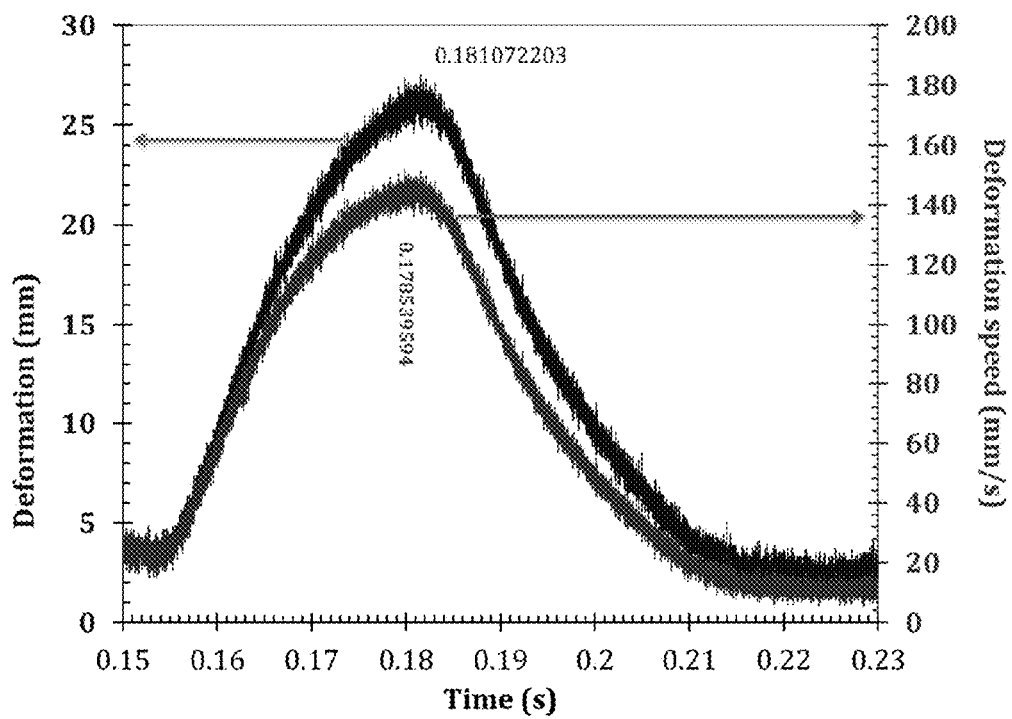
FIG. 5 shows a close-up of FIG. 4 where deformation speed max precedes deformation max by 2.533 ms.
Figure 6:
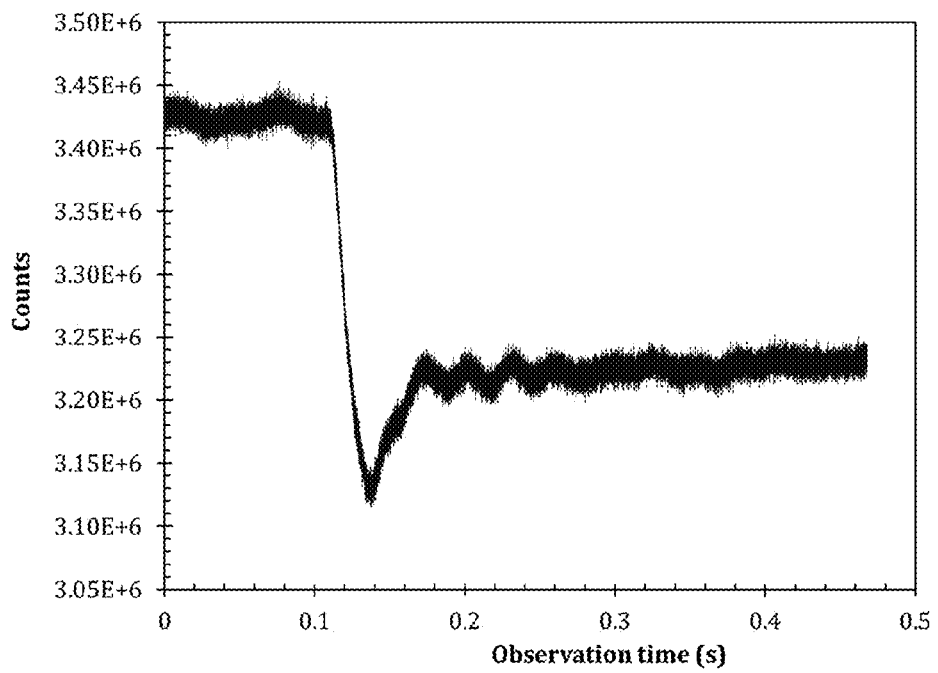
FIG. 6 shows ballistic kinetics of a steel plate.
Figure 7:
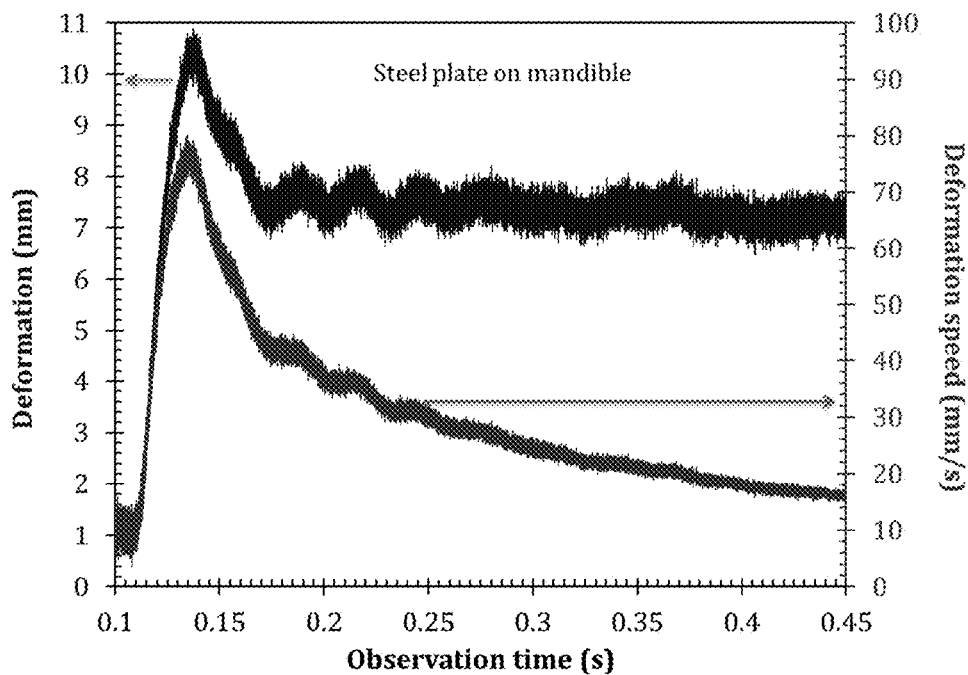
FIG. 7 shows deformation of a steel plate with relaxation and where the pendulum with a pointed head was dropped from 13" height.
Figure 8:
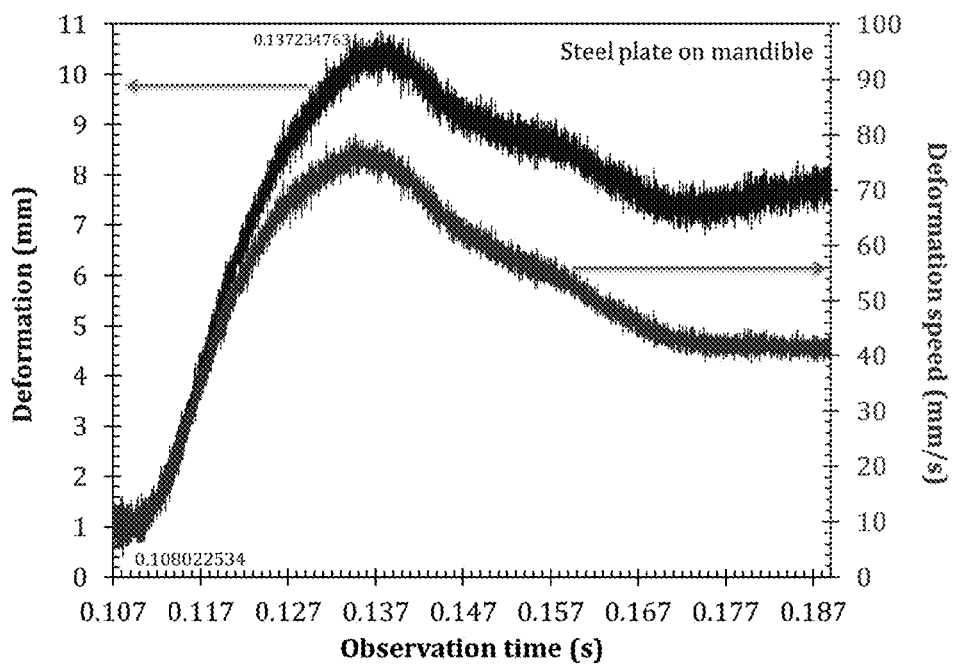
FIG. 8 shows a close-up of FIG. 7 where deformation peak time is ~29 ms and the speed profile is calculated assuming maximum deformation ~10.6 mm.

A close-up of FIG. 4 is shown in FIG. 5, indicating that the deformation propagation speed lags the deformation by about 2.5 ms. FIG. 6 shows the kinetics of a pointed pendulum drop on a steel plate mounted on the mandible. The plate relaxed back from maximum deformation to a position of equilibrium with visible vibrations before reaching stable equilibrium. FIG. 7 shows the calculated deformation (assumed 10.6 mm) and its speed of propagation. Although it seems to be a single slope from the strike point to the first inflection point in FIG. 7, there are actually four distinct slopes before the deformation reaches the maximum. This is indicative of delamination of different layers within the panel under test. This is not visible from the DIC but can be seen only by terahertz kinetics spectrum.

The results presented above demonstrate the capabilities of terahertz reflectometry in capturing real-time kinetics of the ballistic events. The calculated parameters for the two samples are given in Table 1.

TABLE 1

| Sample | Parameter | | | | |
|---|---|---|---|---|---|
| | $l_{max}$ (mm) | $\Delta t$ (ms) | $l_\tau$ (mm) | $\tau$ (ms) | $V_{max}$ (mm/s) |
| Acrylic plate (Plexiglass ®) | 27 | 30 | ~0 | ~38 | ~145 |
| Steel plate | 10.6 | 29 | ~7.5 | ~35 | ~80 |

In case of a Soldier's helmet, an important quantity is the available energy for potential impact to Soldier's head. At the point of impact, this is simply the kinetic energy of the projectile:

$$E_k = \frac{1}{2}m_p V_p^2, \quad \text{Equation (1)}$$

where $E_k$ is the kinetic energy, $m_p$ is the mass of the projectile, and $V_p$ is the impact velocity of the projectile. It has been indicated that the physical quantity that properly expresses the capacity to do work on tissue and cause damage from blunt impact is, "energy." The blunt criterion (BC) may be expressed as a measure to predict head injury from blunt, less-than-lethal projectiles, as $$BC = \ln\left(\frac{E}{T*D}\right), \quad \text{Equation (2)}$$

where E is the impact kinetic energy in Joules, D is the diameter of the projectile in centimeters, and T is the thickness of the skull in millimeters. However, one needs to recognize that, as a projectile (e.g., a bullet) hits the outside of a helmet, the impact causes the inside of the helmet to deform (bulge) inwards, thus imparting energy on a Soldier's head. It is this energy that causes injury. Thus this energy is significantly less than the impact kinetic energy of the projectile on the helmet's outer skin. Thus we recognize that the deformation propagation velocity is the main quantity; the kinetics data (e.g., as shown in FIG. 4) gives this velocity profile accurately.

Some critical issues related to characterization of ballistic events for improved materials for Soldier personal protective equipment such as the helmet and body armor are described herein. A high sensitivity, high speed terahertz dynamic reflectometer is used to measure reflectance kinetics spectra associated with ballistic events in real-time. Critical parameters related to blunt trauma criterion were computed. Other important parameters were extracted from the reflectance kinetics spectrum including dynamic deformation, propagation velocity, final relaxation position, and delamination characteristics. Kinetics spectrum was utilized to compute the deformation profile and the propagation velocity profile via a priori in-lab calibration. In addition, live firing testing was conducted on a multi-layered panel. Calibration of kinetics spectra were conducted for these panels for both deformation and mass change. In general, terahertz (THz) reflectance kinetics spectra are applied for ballistic event characterization.

The theoretical requirements of ballistic characterization of less-than-lethal impact, the so called blunt criterion, is presented initially. An experimental setup and its calibration for quantifying deformation from kinetics spectrum is then discussed. After that, an in-lab experiment is presented that illustrates the procedure for analyzing kinetics spectrum. A live firing shot on a given panel made of materials used for the helmets is then presented.

Quantitative Requirements for Ballistic Characterization

In case of a Soldier's helmet, an important quantity is the available energy for potential impact to the Soldier's head leading to trauma or injury. Therefore, an important requirement is the quantification of this energy, $E_{trauma}$. At the point of impact, the kinetic energy, $E_k$, of the projectile is simply (Equation 1 repeated below):

$$E_k = \frac{1}{2} m_p V_p^2,$$ Equation (1)

where, $m_p$ is mass of the projectile, and $V_p$ is impact velocity of the projectile. The physical quantity properly expressing the capacity to do work on tissue and cause damage from blunt impact is "energy." The blunt criterion (BC) is a measure to predict head injury from blunt, less-than-lethal projectiles, as (Equation 2 repeated):

$$BC = \ln\left(\frac{E}{T*D}\right),$$ Equation (2)

where E is the impact kinetic energy in Joules, D is the diameter of the projectile in centimeters, and T is the thickness of the skull in millimeters. One needs to recognize that, as a projectile (e.g., a bullet) impacts the outside of a helmet, this causes the inside of the helmet to deform (bulge) inwards, thus imparting energy to the Soldier's head. It is this energy that causes trauma or injury; which is less than the impact kinetic energy ($E_k$) of the projectile on the helmet's outer skin. Eq. (2) therefore takes the form, $$BC = \ln\left(\frac{Etrauma}{T*D}\right).$$ Equation (3)

The deformation propagation velocity obtained from the kinetics data gives the velocity profile from which $V_{max}$ for the helmet interior surface is calculated. However, $$E_{\downarrow}trauma = \frac{1}{2} m_{\downarrow}eff V_{\downarrow}max^{\uparrow}2,$$ Equation (4)

where, $m_{eff}$ is the effective mass of the deformed portion of the helmet. Knowing $m_{eff}$ one can quantify the energy of BC. However, neither DIC nor X-ray can determine $m_{eff}$ because, while the density may be approximated from the known material properties and the effective area (volume) may be estimated from the post-firing device under test (DUT), the effective mass of trauma generating volume is still not determined. Since the helmets are made from multi-layered material, one needs to know delamination characteristics and possible loss of material during impact. Thus $m_{eff}$ must be determined experimentally. Since terahertz radiation can penetrate the helmet material, it is possible to determine any mass loss/gain due to impact. In this case, calibration of material mass as a function of THz transmission must be done a priori.

Figure 9:
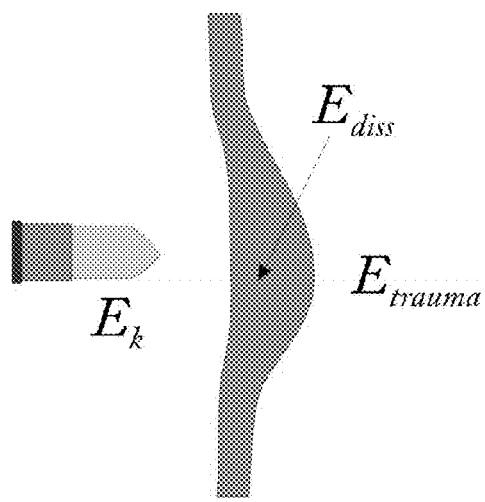
FIG. 9 shows that an incident energy is the sum of trauma generating energy and dissipated energy: $E_k = E_{trauma} + E_{diss}$.

In light of the foregoing, the total energy delivered by the projectile is then comprised of two components: $E_k = E_{trauma} + E_{diss}$, where $E_{diss}$ is the energy dissipated by the helmet material (see illustration in FIG. 9). While it can be easily assumed that $E_{diss} = E_k - E_{trauma}$, the nature of $E_{diss}$ has some interesting connotations. Since the helmet is made of a multi-layered material, $E_{diss}$ is not likely to be just the heat energy. It is hypothesized that ballistic impact may generate shock waves which may also contribute to trauma. In either case, the net effect of a ballistic impact, under BC criteria, is the trauma generating energy $E_{trauma}$, and thus, $E_{trauma}$ is still dependent on $m_{eff}$ which must be measured. The THz reflectometry provides an opportunity to quantify $m_{eff}$.

Figure 10:
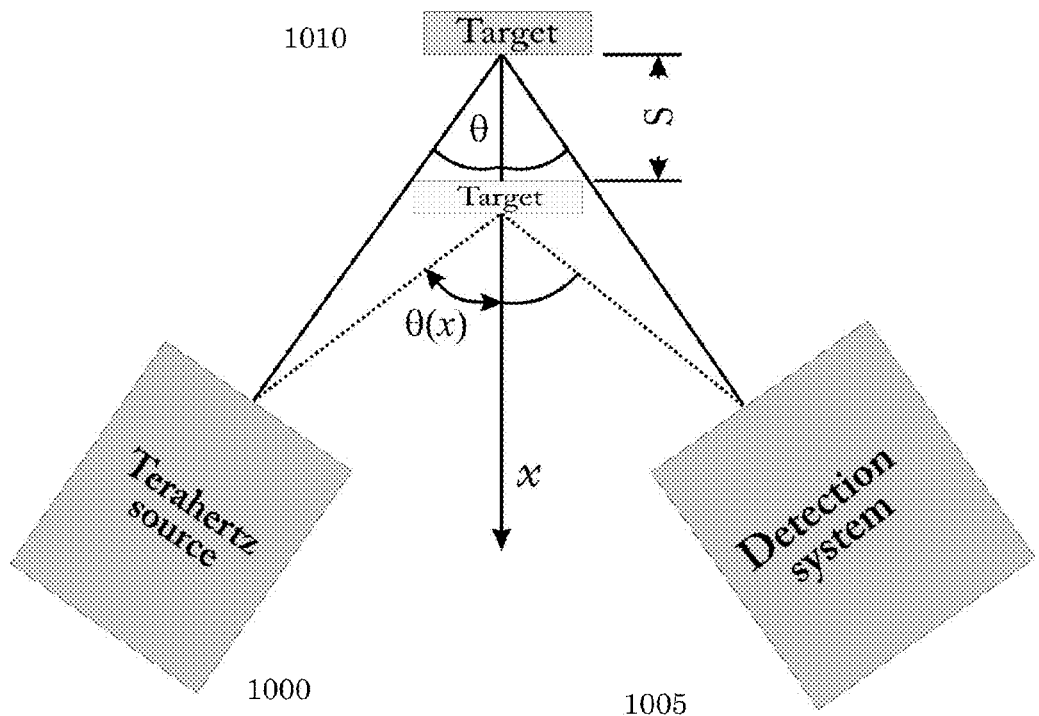
FIG. 10 shows an example arrangement for a terahertz dynamic reflectometer (TDR)

FIG. 10 shows an experimental setup for real-time in-situ ballistic kinetics measurements. An electro-optic dendrimer based terahertz source 1000 generates terahertz radiation up to ~35 THz. The source 1000 and the detection units 1005 remain stationary and are oriented at angle θ=35°. As the target 1010 moves from its initial position along the x-axis, both θ and the deformation (S) become position dependent; θ→θ(x) and S→S(x). Thus the reflected power is a function of x that can be described by the Fresnel's law. A controlled measurement of power vs. displacement then serves as a measure of deformation for a given surface corresponding to the measured kinetics spectrum at a specific angular orientation and other alignment conditions. Once aligned, the configuration must remain fixed in order the calibration to remain valid. For any change of the experimental conditions or the target surface, a new calibration must be conducted.

Figure 11:
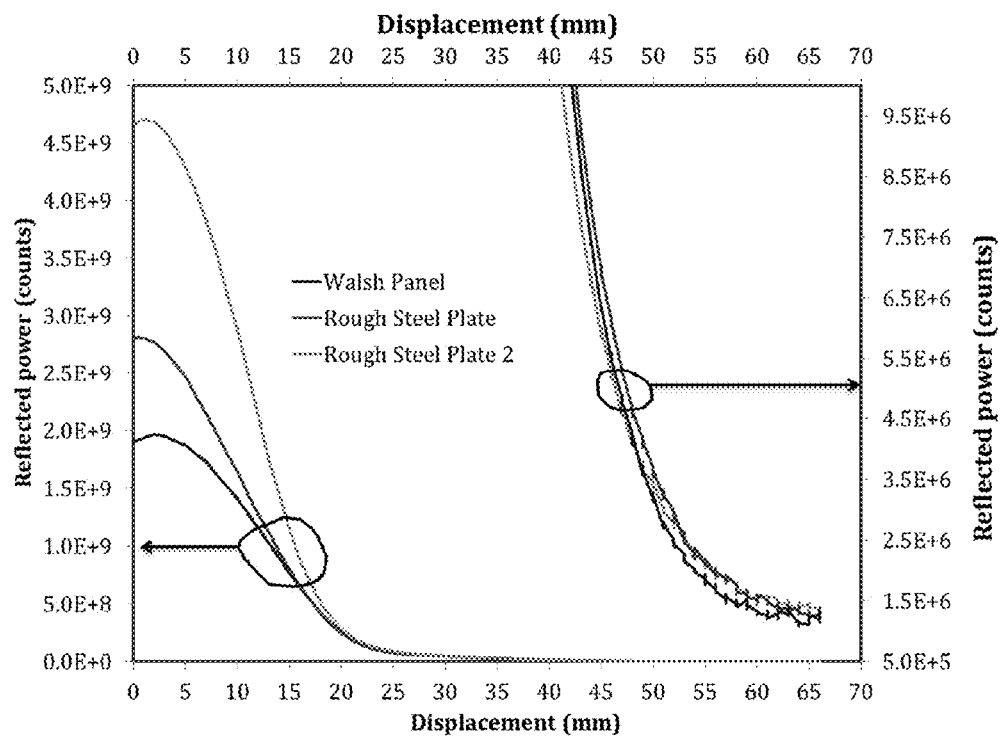
FIG. 11 shows a calibration of deformation (displacement) vs. power.
Figure 12:
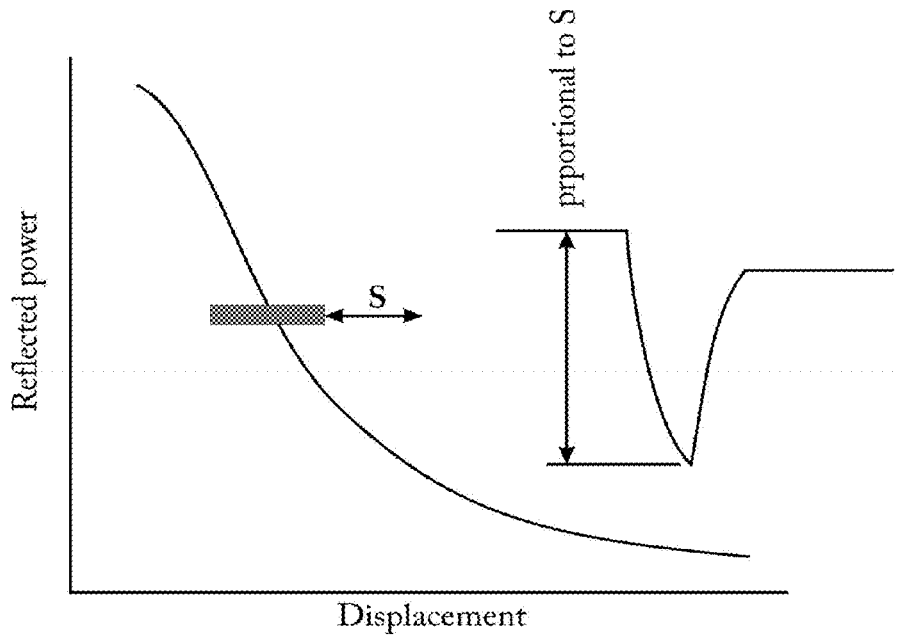
FIG. 12 shows a displacement curve with respect to a target.

FIG. 11 shows the calibration curve for three different target materials. Here the reflected power (counts) has been measured as a function of displacement. Each of these curves will serve as a "look-up" table for quantifying the deformation of the corresponding material for a given ballistic impact kinetics spectrum. This is illustrated in FIG. 12, where the kinetics of a ballistic event is recorded and the deformation is then read-off of the corresponding calibration curve. When a target is placed at a fixed position within the limits of its calibration, the measured power remains unchanged. A sudden displacement of the target or a deformation on a localized section where the THz beam is incident causes the power to drop proportional to the displacement and then becomes steady again at the new position (shown in inset of FIG. 12). The power vs. time curve (kinetics spectrum) allows quantification of the deformation from this curve.

While the curves on the left Y-axis tend to go to zero at displacement 30 mm and above, however, when the Y-axis is expanded (right Y-axis), the reflected power is still a rapidly varying function of displacement. This indicates that that the calibration is valid for displacements up to at least 60 mm. The concept is further illustrated in FIG. 12. When a target is placed on the displacement curve shown, the measured power remains steady as long as the target remains fixed. A sudden displacement (deformation) of the target cause the power drop proportional to the displacement and then becomes steady at the new position. Therefore, the power measured in real-time generates a kinetics curve (inset) from which corresponding displacement can be quantified.

Described herein is deformation and velocity profile.

Figure 13:
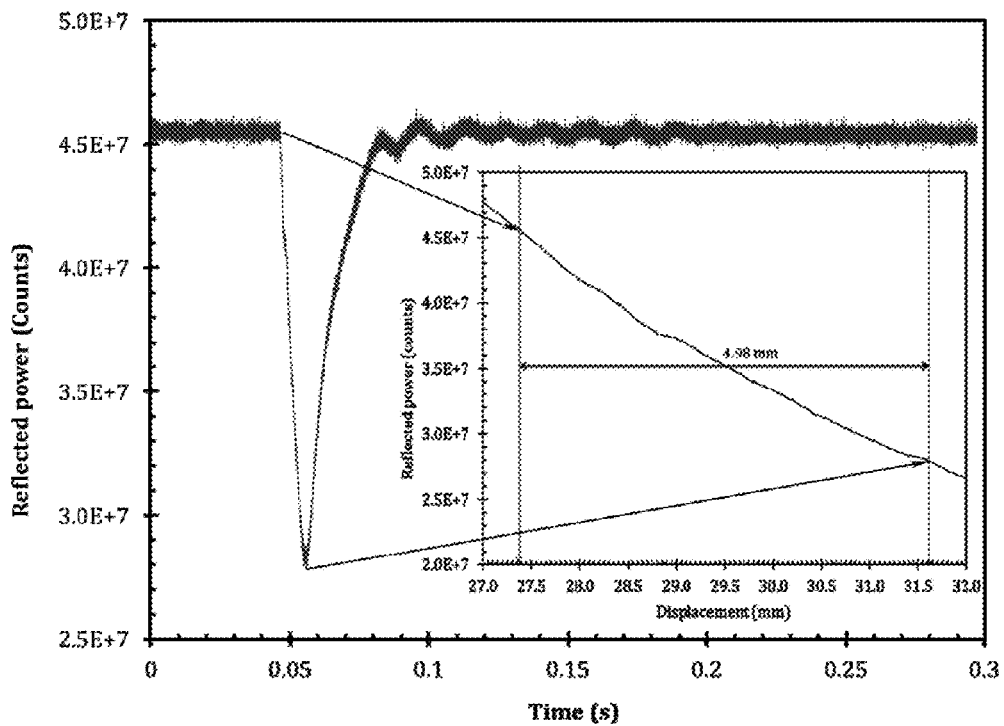
FIG. 13 shows an example real-time kinetics spectrum.

FIG. 13 shows the kinetics spectrum of an in-lab demonstration of the principle discussed above. Here, a rough steel plate was mounted at position within the limits of calibration of the same material. A small hammer was used to strike the plate while its time dependent reflected power was captured at a high speed. The time interval between successive points is $5.94 \times 10^{-6}$ s (time resolution of the system). The special resolution is better than 1 μm, the calibration measurement was done at every 200 μm. The calibration graph was utilized to read off the displacement 4.98 mm (see insert of FIG. 13).

Figure 14:
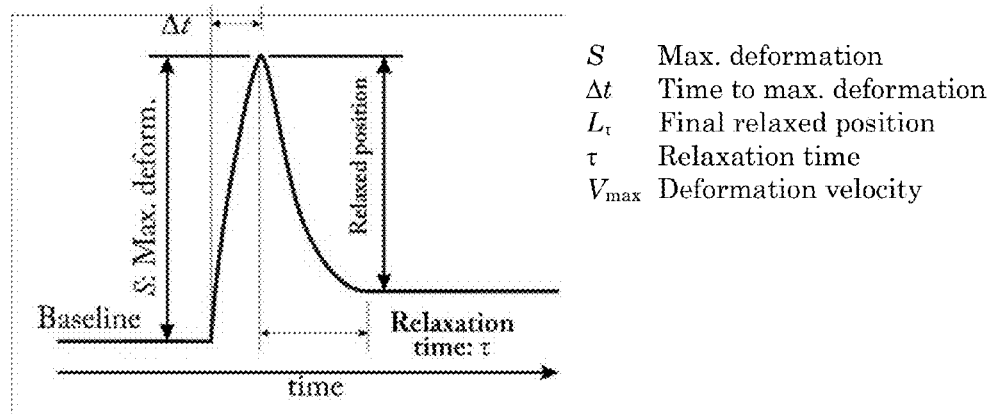
FIG. 14 shows an example definition of parameters extracted from the kinetics spectrum.

Once the deformation is read-off of the kinetics spectrum, the following quantities may be extracted; which will be used to further characterize different candidate materials. These may include maximum deformation (S), Time to max deformation (Δt), Position of the final relaxed state ($l_r$), Relaxation time, τ, and deformation speed (υ). These parameters are illustrated in FIG. 14 and Table 2.

TABLE 2

| Sample | $l_{max}$ (mm) | Δt (ms) | $l_r$ (mm) | τ (ms) | $V_{max}$ (mm/s) |
|---|---|---|---|---|---|
| Plexiglas [1] | 27 | 30 | ~0 | ~38 | ~145 |
| Steel plate [1] | 10.6 | 29 | ~7.5 | ~35 | ~80 |
| Walsh panel | 10.4 | 1.8 | ~10 | — | ~140000 |

Velocity Calculation

Once the maximum displacement is read-off of the kinetics spectrum utilizing the calibration curve (FIG. 11), the deformation propagation profile is calculated from the spectrum. From this profile the next parameter to calculate is the speed of deformation. Here the following boundary conditions are utilized.

Initially the target is at rest; therefore, the initial velocity is zero. As the deformation propagates, the propagation accelerates and then at the maximum deformation the velocity is again zero. If the target recoils (in the opposite direction), the velocity again increases and then comes to zero when the target stops at the relaxed position. So one can utilize the Newton's laws for uniformly accelerated motion:

$$S = V_o t + \frac{1}{2}at^2 \quad \text{Equation (5)}$$

$$\text{Since } V_o = 0, \rightarrow S = \frac{1}{2}at^2$$

$$\text{Or, } a = \frac{2S}{t^2}(5) \quad \text{Equation (6)}$$

Knowing a, one can determine v from, $$V^2 - V_0^2 = 2aS \quad \text{Equation (7)}$$

Figure 15:
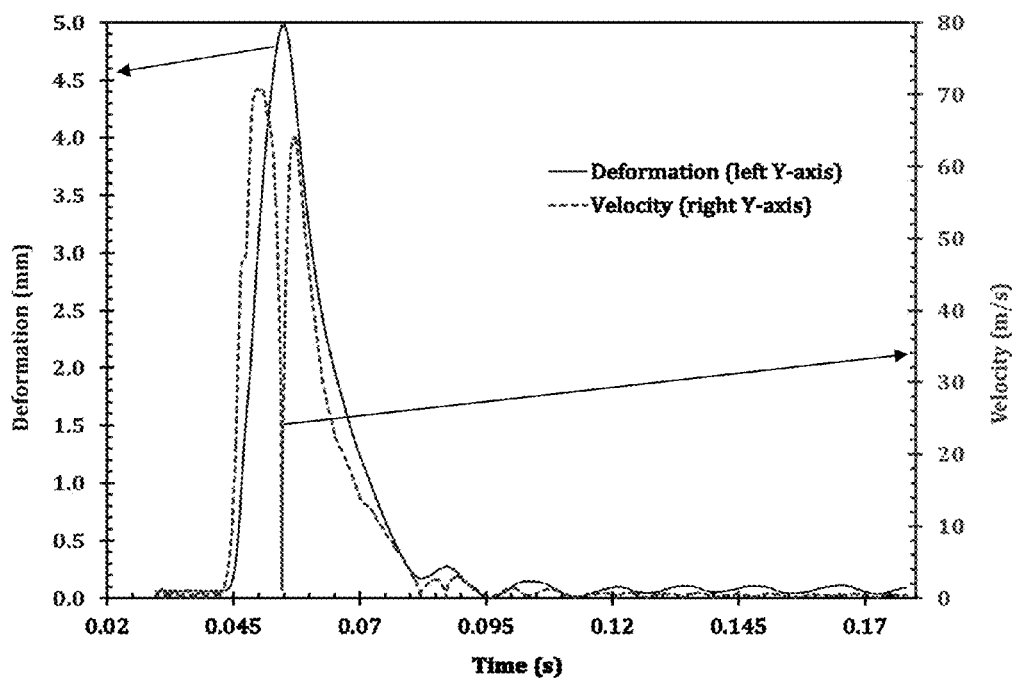
FIG. 15 shows a deformation (left Y-axis) profile calculated from the kinetics data of FIG. 13 with a depth of 4.98 mm and a calculated velocity profile of deformation is shown on a right Y-axis.

FIG. 15 displays the calculated deformation profile from the kinetics spectrum (FIG. 13) and the velocity profile calculated from Equation (7). Here the kinetics spectrum was denoised and then a moving average was adapted for calculating quantities in FIG. 15.

Additionally, a life firing test was conducted. Kinetics spectrum of a multilayered panel, shown in FIG. 16, was captured using the same setup as before (FIG. 10). Since the deformation calibration for this sample was not done ahead of time, the information available from a simultaneous DIC measurement was used to calculate the profiles for deformation and propagation velocity as shown in FIG. 17.

Figure 18:
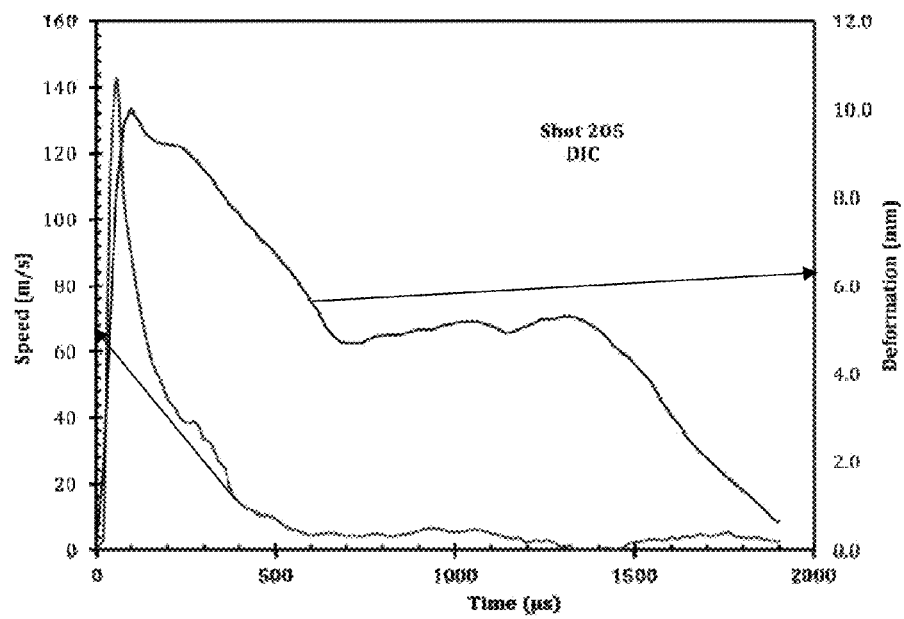
FIG. 18 shows digital image correlation (DIC) data that the deformation recoils to the final distance <1 mm and that this is in contradiction with the real situation where the deformation remains as indicated by the THz data.

FIG. 18 shows DIC data that the deformation recoils to the final distance <1 mm. This is in contradiction with the real situation where the deformation remains as indicated by the THz data.

Figure 16:
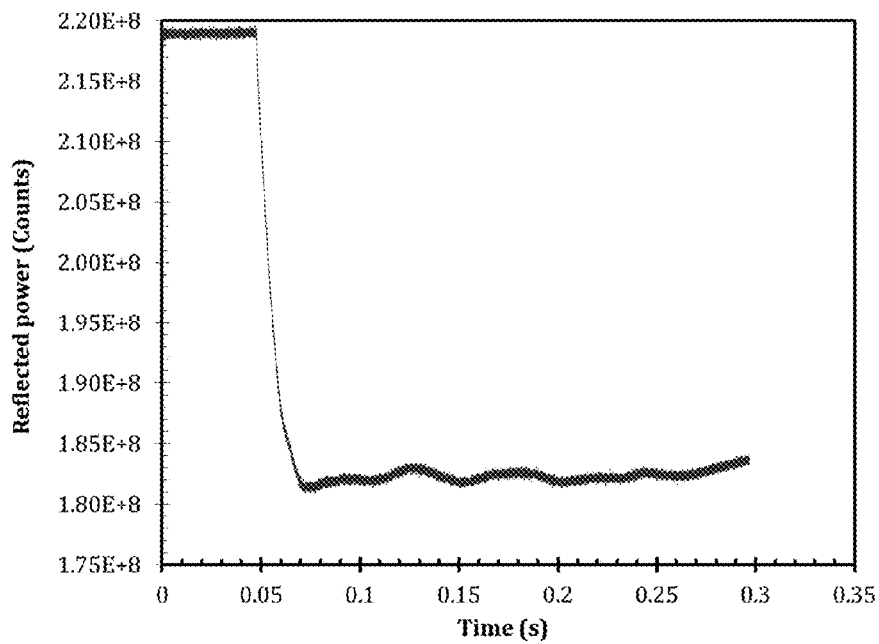
FIG. 16 shows a kinetics spectrum of a live shot indicating that the target underwent permanent deformation, where the wavy nature at the tail end most likely occurred from the vibrations of the mounting platform.
Figure 17:
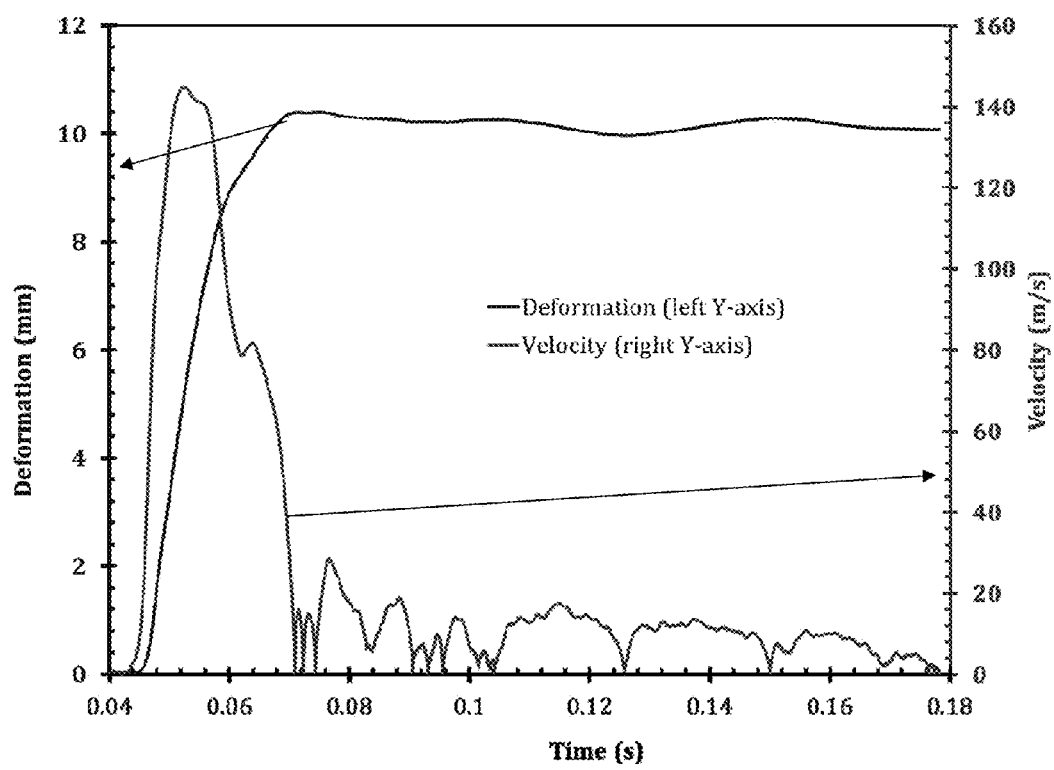
FIG. 17 shows a deformation profile (left Y-axis) calculated from the kinetics spectrum of FIG. 16 with a depth of 10.4 mm and a calculated velocity profile of deformation is shown at a right Y-axis.
Figure 19:
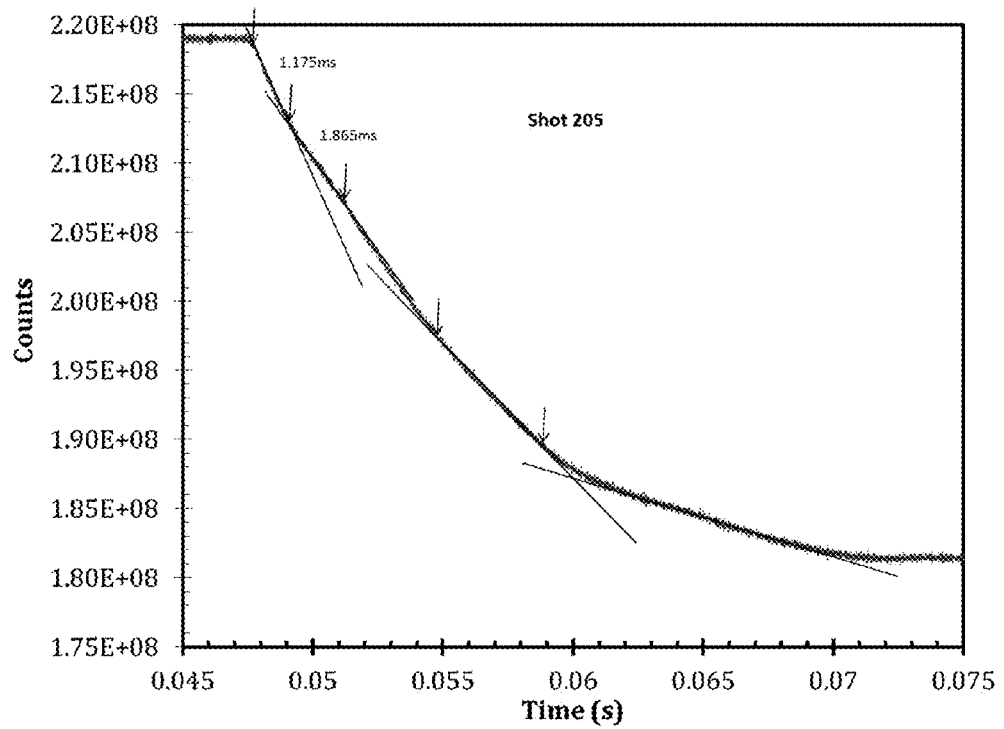
FIG. 19 shows a close-up of the kinetics spectrum of FIG. 16.

FIG. 19 shows a close-up of kinetics spectrum of FIG. 16. Although in FIG. 16 it appears to be a single slope from the strike point to the first inflection point, there are actually four distinct slopes before the deformation reaches the maximum. This is indicative of delamination of different layers within the panel under test. This is not visible from the DIC but can be seen only by terahertz kinetics spectrum.

Mass Calibration

The effective mass $m_{eff}$ (Equation (4) or change in mass) may be read off of the mas vs. transmission calibration. The governing principle here is Beer-Lambert's law. Ordinarily, Beer-Lambert's law is used to determine the concentration dependence, C, of a solute in a solvent from absorbance (A) data: A=ε lC, where l is the path length and ε is the extinction coefficient (or molar absorptivity). However, for a ballistic impact, all material parameters may be assumed fixed, with the path length l being replaced by mass, m, due to delamination. Since the transmittance (T) is proportional to the variation in path length, or equivalently, the mass change, measurement of T(t) can yield the dynamics of mass change.

The thickness value may be converted to mass for known geometry and material properties. However, for a composite material such as the Walsh panel the ab initio calculation is not possible, one must resort to a number of approximations. Therefore, an effective means is to calibrate the transmitted power as a function of material thickness or equivalently the mass. This can only be done if the material permits transmission of energy through it. Consequently only terahertz is feasible for non-metallic samples. While X-ray will also penetrate these materials however, X-ray lacks the sensitivity required for this situation.

Figure 20:
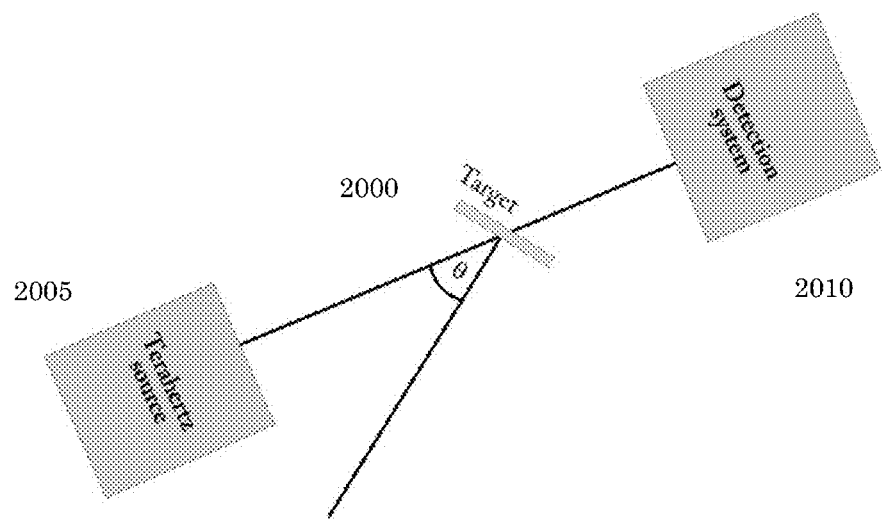
FIG. 20 shows an example arrangement for mass vs. transmission calibration.

For the mass calibration the setup in FIG. 20 was used. Here, a target 2000, a terahertz source 2005 and detection system 2010 were organized such that the projectile path remains clear. With this orientation the source 2005 and the detection system 2010 is aligned such that the detector 2010 received maximum power. Walsh panel, mounted on a fixed platform, was then introduced in the beam path and the initial power was recorded. Then a thin layer of the panel was peeled off and transmission was measured again. This way transmitted power was recorded while thin layers of the panel were removed successively. For each layer removed, a small disk was cut from the layer (approximately equal to the beam spot) and its mass was measured on a micro balance.

Figure 21:
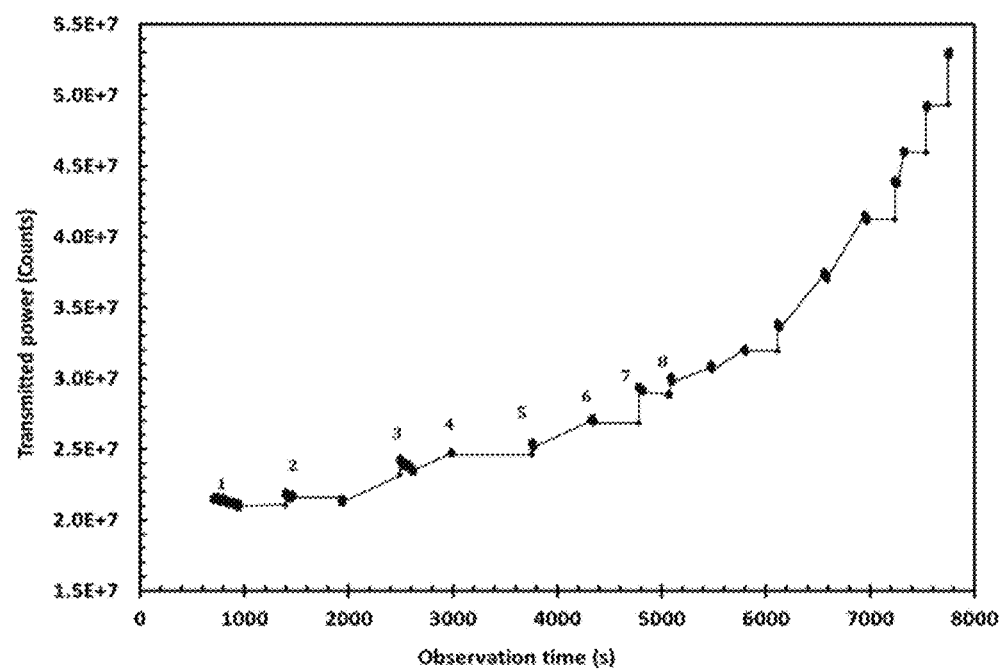
FIG. 21 shows that transmitted power increases as the successive layers are removed from a panel.
Figure 23:
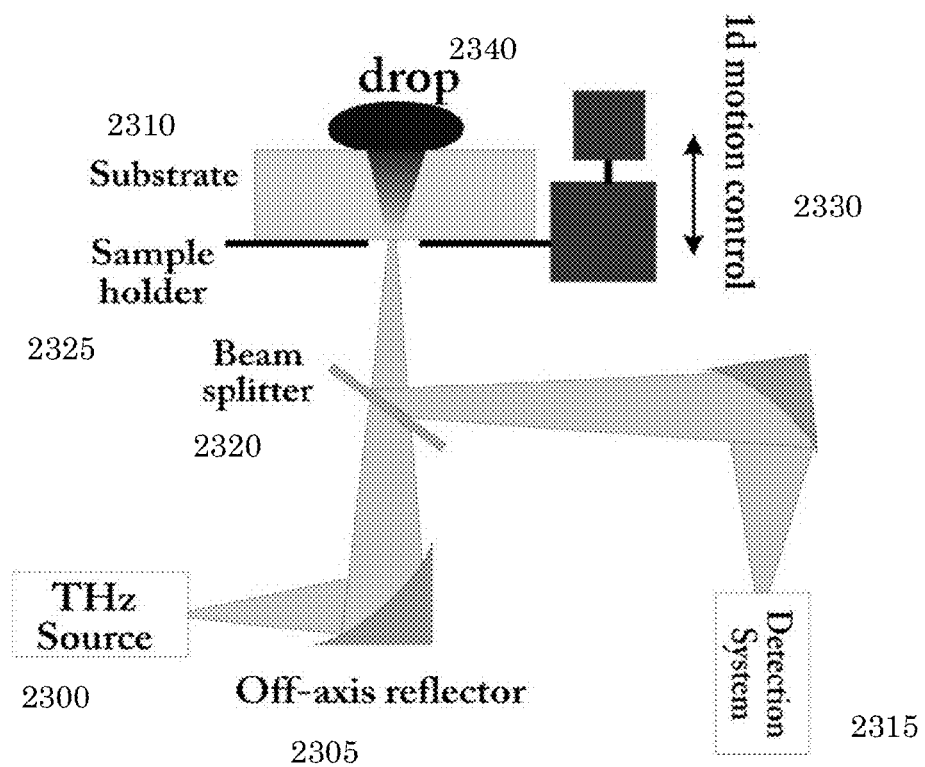
FIG. 23 shows an example architecture for a terahertz scanning reflectometer.
Figure 24:
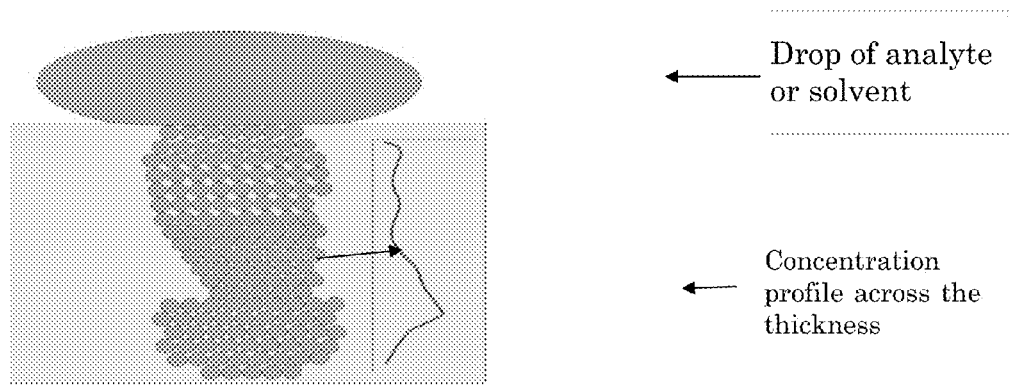
FIG. 24 shows molecules permeating in to substrate.

FIG. 21 shows the successive layers' mass dependence of the transmitted power. FIG. 23 shows the measured power vs. measured mass of the disks cut out of the peeled layers. This will serve as the calibration for determining mass change during the ballistic impact. This calibration must be done a priori for a given geometry and for a given material.

Figure 22:
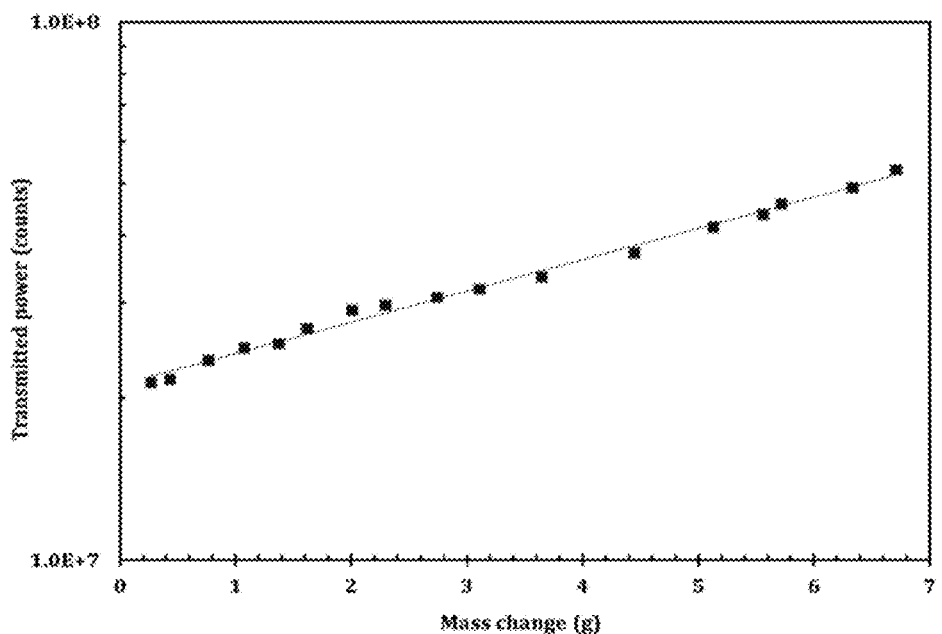
FIG. 22 shows transmitted power plotted as a function of cumulative mass removed from the panel.

To determine the trauma generating mass (effective mass, $m_{eff}$) one may utilize the calibration curve shown in FIG. 22. Alternatively, the curve may be digitized by fitting a suitable equation and then $m_{eff}$ may be calculated from measured transmission kinetics spectrum.

A terahertz dynamic reflectometer (TDR) has been used to capture real-time kinetics spectrum of ballistic events. Testing was done on prototypes to demonstrate applicability of the TDR in real ballistic event characterization. Critical parameters such as maximum deformation, deformation propagation velocity, deformation time, relaxation time, and final relaxed position can be accurately determined from the kinetics spectrum. The physical principle and requirements for analyzing Soldiers' helmet and body armor has been described in light of less-than-lethal ballistic impact i.e., the blunt criterion. The formulation for calculating deformation, deformation propagation velocity and mass change has been validated by in-lab experiments. In addition, live firing data have been analyzed. Kinetics spectra from reflection measurement have been analyzed for deformation and its propagation velocity. The kinetics spectra from transmission measurements may be analyzed for any mass change during ballistic impact due to delamination or material evaporation. An example of mass calibration has been provided from which the change in mass may be quantified when a corresponding transmission kinetics spectrum is recoded. In the future in-situ calibration will be conducted to quantify the parameters for the blunt criteria discussed herein.

Terahertz reflectometry and spectrometry is used to investigate the permeation kinetics and concentration profile of active ingredients in to the stratum corneum. This is a direct, non-invasive, and real-time measurement of kinetics and concentration gradient of analytes in to the stratum corneum. Moreover, this is a general method that is applicable to any substrate and analyte combinations. It was found that the analyte concentration in stratum corneum of 1% hydrocortisone solution in propylene glycol is significantly higher than 1% caffeine in deionized water. These findings are important for quantifying transdermal drug delivery formulation with these solvents and can be extended to other analytes and solvents. Terahertz spectra of untreated stratum corneum vs. those treated with 10 mM N-0915 (see FIG. 33 for chemical formula) solution were distinctively different. Additionally, the N-0915 treated specimen exhibits prominent absorption peaks in the 7.27 THz, 11.88 THz and 18.42 THz region while the spectrum of blank specimen exhibits a monotonous increase of absorbance with frequency. This indicates the importance of broadband terahertz spectroscopy of a range of 20 THz or more to be able to probe molecular events.

Described herein are methods and apparatus for examining transdermals/topicals and cosmetic formulations via terahertz spectroscopy and terahertz scanning reflectometry. Transdermals and topicals often involve use of compounds that either enhance or retard the permeation of the active ingredients across the skin. The agents that enhance the permeation of the actives across the skin are termed as permeation enhancers and the agents that slow down the penetration of the active are known as retardants. Permeation enhancers play a great role in increasing the bioavailability and efficacy of therapeutic agents by compromising the barrier properties of the skin and lead to enhancement in the delivery of the active across the skin. On the other hand, the retardants help in limiting the skin absorption of agents such as agrochemicals (pesticides), chemical warfare agents, mosquito repellants, sunscreens and household chemicals that have the attributes of easily permeating through the barrier of the skin.

Many formulations used in transdermal and topical drug delivery use water and/or propylene glycol as solvents or penetration enhancers. The permeation of two compounds in the stratum corneum are described herein: (i) hydrocortisone dissolved in propylene glycol (PG), and (ii) caffeine dissolved in water.

Propylene glycol(1,2-propanediol) is a diol with chemical formula $C_3H_8O_2$. It is a colorless, nearly odorless, clear, viscous liquid used as a solvent in many pharmaceuticals, moisturizers, hand sanitizers, and antibacterial lotions. Propylene glycol is used as a vehicle for penetration enhancers but is also considered a penetration enhancer in its own right. It permeates through the stratum corneum (SC) that alters the thermodynamic activity and partitioning of associated drug. Water is a common solvent; the water content of human stratum corneum is typically around 20% of the tissue dry weight but by soaking or occluding the skin, the stratum corneum water content can reach up to 400% of the tissue dry weight. Increased hydration can lead to increased permeation of associated drug as free water within the tissue alters the solubility of drug and therefore partitioning into the skin.

Additionally, terahertz spectroscopy was conducted on SC specimen that was treated with an active ingredient (N-0915). The spectra of blank SC and those saturated with N-0915 are also reported.

Experimental Method

The measurements were carried out on a terahertz scanning reflectometer as described herein and the experimental setup is shown in FIG. 23. A CW terahertz source 2300 is used that generates terahertz radiation from an electro-optic dendrimer via difference frequency methods as described in for example, in U.S. Ser. No. 13/281,230, filed Oct. 25, 2011, which is a divisional of U.S. Ser. No. 11/862,474, filed Sep. 27, 2007, which issued as U.S. Pat. No. 8,050,531 on Nov. 1, 2011, which claims the benefit of U.S. Provisional Application No. 60/827,206, entitled "Electro-Optic Dendrimer, Electro-Optic Sensor, THz Waveguide, and Production Thereof, filed Sep. 27, 2006; and a continuation-in-part of U.S. Ser. No. 12/322,662, filed Feb. 5, 2009, which claims the benefit of U.S. Provisional Application Ser. No. 61/026,233, filed Feb. 5, 2008 and entitled "Terahertz Time Domain and Frequency Domain Spectroscopy" and is a continuation-in-part of U.S. patent application Ser. No. 11/862,473, filed Sep. 27, 2007, and entitled "Dendrimer Based Electro-optic Sensor", which was published as U.S. 20080128618 on Jun. 5, 2008 and U.S. patent application Ser. No. 11/862,474, filed Sep. 27, 2007, and entitled "Dendrimer Based Terahertz Generator", which was published as U.S. Publication No. 2008/0099698 on May 1, 2008, all of which are herein incorporated in their entireties. The terahertz beam is focused on to a substrate 2310 at a 90° angle via an off-axis parabolic reflector 2305 (normal incidence). The beam reflected by a substrate 2310 is directed to a detection system 2315 via a beam splitter 2320. The specimen cell is comprised of a sample holder/platform 2325 that is controlled by a motion controller 2330, which may be a 1D, 2D or 3D motion controller. An imaging system may be included to generate images from the generated spectrum.

Figure 25:
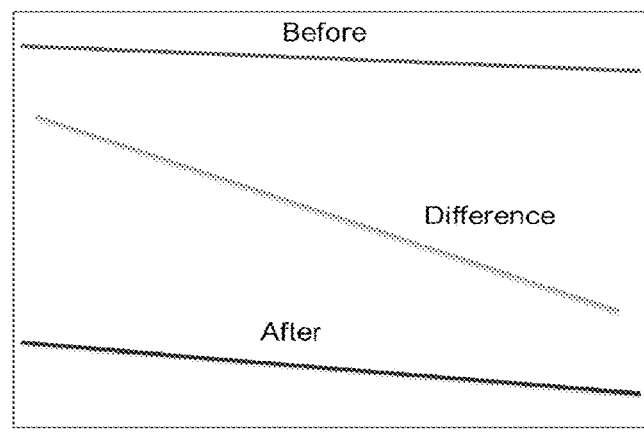
FIG. 25 shows computation of analyte concentration from scan of blank (before) and saturated substrate (after)
Figure 26:
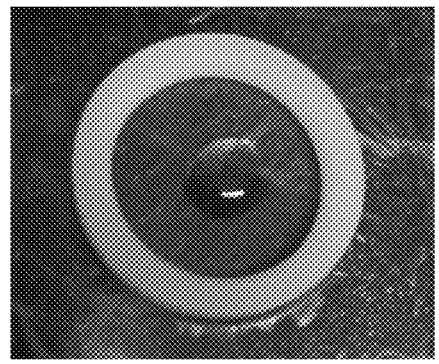
FIG. 26 shows human stratum corneum mounted on the sample holder on which a drop is applied.

The off-axis parabolic reflector 2305 is adjusted such that initially the terahertz beam remains focused on the substrate surface 2310. At this position the motion control 2330 is engaged to move the focal point inside the substrate 2310 to interrogate the reflectance across the thickness; this gives the $$\frac{\partial C}{\partial x}$$

when the blank substrate reflectance is subtracted from the reflectance of the same substrate treated with a desired ingredient (as shown in FIGS. 25 and 26), $$\left|\frac{\partial C}{\partial x}\right|_{ANALYTE} = \left|\left|\frac{\partial C}{\partial x}\right|_{BEFORE} - \left|\frac{\partial C}{\partial x}\right|_{AFTER}\right| \quad \text{Equation (8)}$$

However, when the beam remains focused at the surface and the motion control 2330 is locked at that position, then an ingredient 2340 may be applied on the substrate 2310 to let it permeate across the thickness while the reflectance is measured in real time. In this case the reflectance is directly proportional to the rate of permeation of the ingredient across the substrate 2310, $$\frac{\partial C}{\partial t}.$$

Analysis was carried out on two batches of dermatomed human skin samples supplied from the Human Skin Bank in New York City, N.Y. The stratum corneum (SC) was separated using known heat separation techniques. Two model compounds were selected, namely, hydrocortisone and caffeine. The former represented a lipophilic compound and the latter a hydrophilic one. Solutions for analysis (DI $H_2O$, propylene glycol [PG], 1% hydrocortisone in PG, and 1% caffeine in DI $H_2O$) were supplied by Rutgers University. Measurements were taken using a TeraScan® unit from Applied Research and Photonics, Inc. (Harrisburg, Pa.). A stratum corneum specimen 2500 mounted on the cell 2505 is shown in FIG. 25. After all measurements were recorded, the results were imported to Microsoft Excel for visualization and analysis.

Primary goals included: measuring the rate at which a given analyte diffused through SC; and measuring the depth permeated by the analyte after stabilization (saturation).

Samples of SC were cut into squares large enough to cover a 5.31 cm$^2$ circle cut into a 5×5 cm Plexiglass® slide and fixed by the SC's inherent adhesiveness as shown in FIG. 26. All SC samples were oriented with the external facing upwards; they were fixed on the cell by a Teflon ring. The cell was then mounted in the TeraScan® reflectometer.

All SC samples that were to receive an analyte solution were vertically scanned to assess their reflectance at increasing depths; this was performed on all samples as a control before application of the analyte. Permeation kinetics, i.e., the rate at which a solution penetrated the SC, were recorded after dropping 200 µL of solution from an adjustable micro-pipette with the drop centered directly over the focal point. Permeation was considered complete after the kinetics reached a steady state. The solution was then pipetted off, and the remainder (on top) was carefully absorbed with a cotton swab. A second set of scans were performed to assess the concentration gradient of the analyte across the depth of the substrate. In all cases at least 3 runs were taken, average of which is utilized for subsequent analysis.

Figure 27:
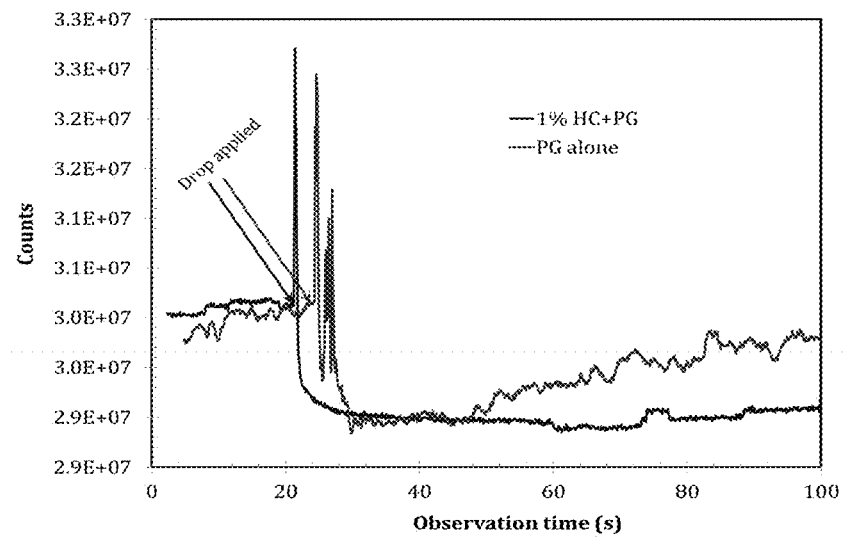
FIG. 27 shows kinetics of permeation of two solutions in to stratum corneum (close-up view)
Figure 28:
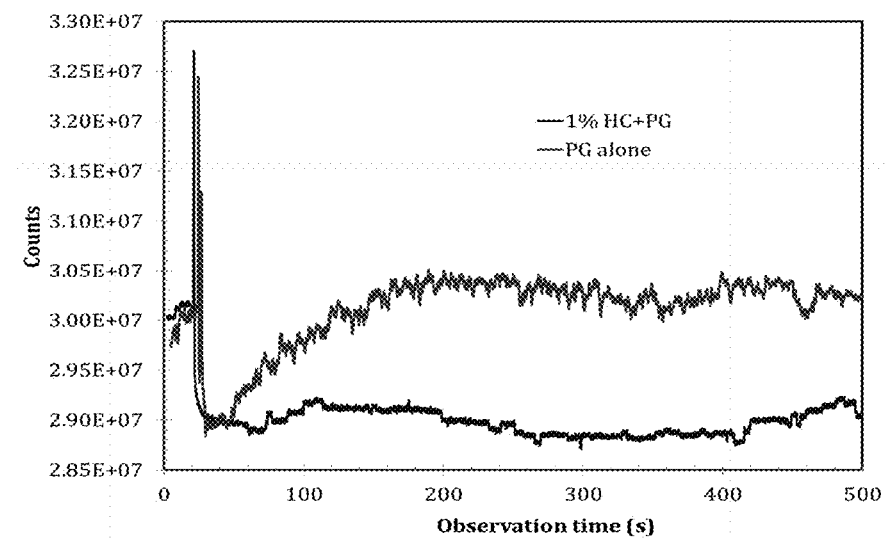
FIG. 28 Kinetics of permeation of two solutions in to stratum corneum over longer time.
Figure 29:
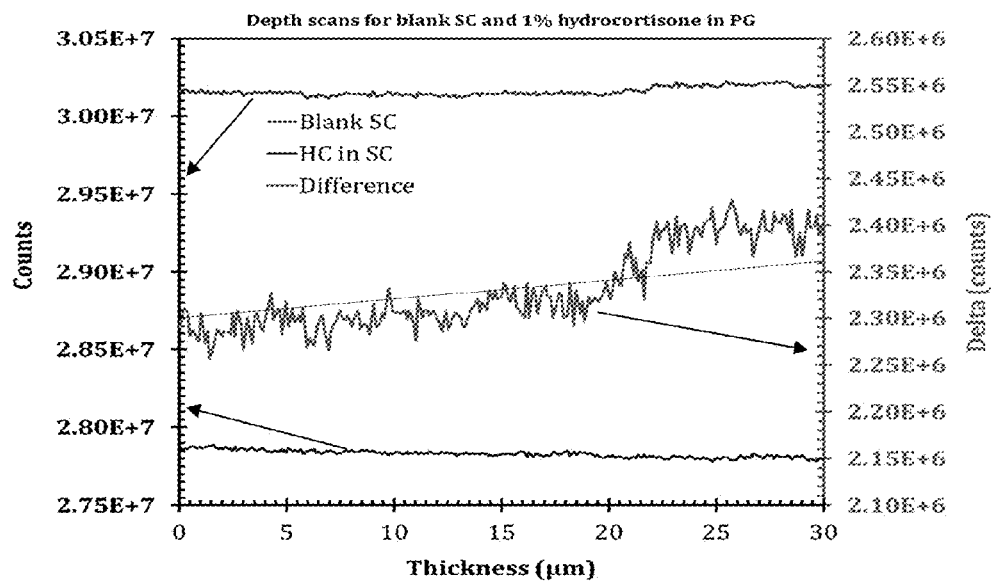
FIG. 29 shows a depth scan of stratum corneum.

A pure sample of PG was tested as a blank for its permeation kinetics through SC as shown in FIG. 27. This kinetics was later compared with that obtained for the hydrocortisone solution in PG. Upon the completion of kinetic measurement (i.e., when the kinetics reached saturation), its depth scan was run and the data stored in a file. Then a fresh specimen of SC was mounted. Three depth scans were performed on the blank stratum corneum. The average of these three runs is shown in FIG. 29 (marked "Blank SC"). Kinetics measurement was then carried out with a solution of 1% hydrocortisone in PG as shown in FIG. 27. FIG. 28 shows a close-up view of the data shown in FIG. 27. After removal of analyte from the SC upper surface, three more depth scans were performed to assess the analyte's depth of permeation (as shown in FIG. 29, marked "HC in SC"). FIG. 29 shows a depth scan of stratum corneum. Top is a scan of blank SC and bottom is a scan after the SC is saturated by 1% hydrocortisone solution in propylene glycol. The middle curve (right y-axis) is the difference of the top and the bottom curves indicating the distribution of the hydrocortisone solution across the SC.

Figure 30:
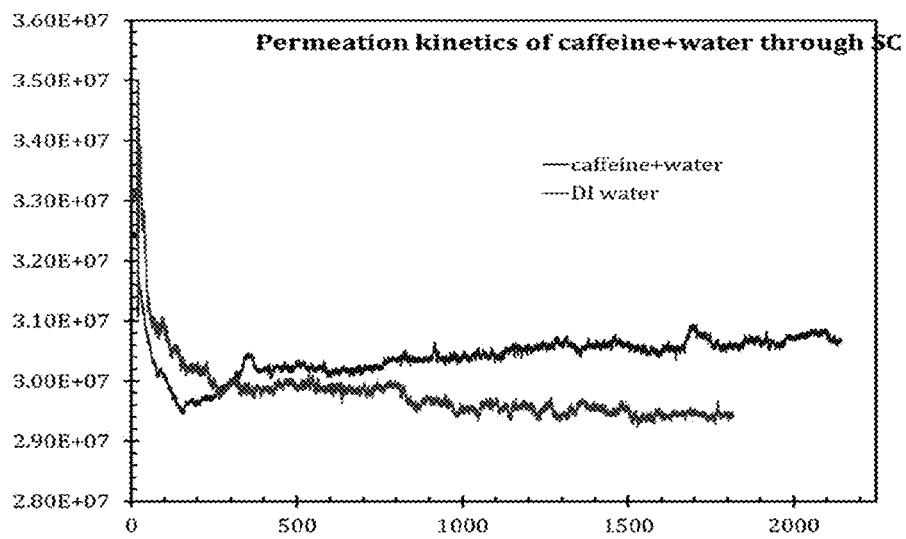
FIG. 30 shows a permeation kinetics of DI water and 1% caffeine in DI water in the stratum corneum.
Figure 31:
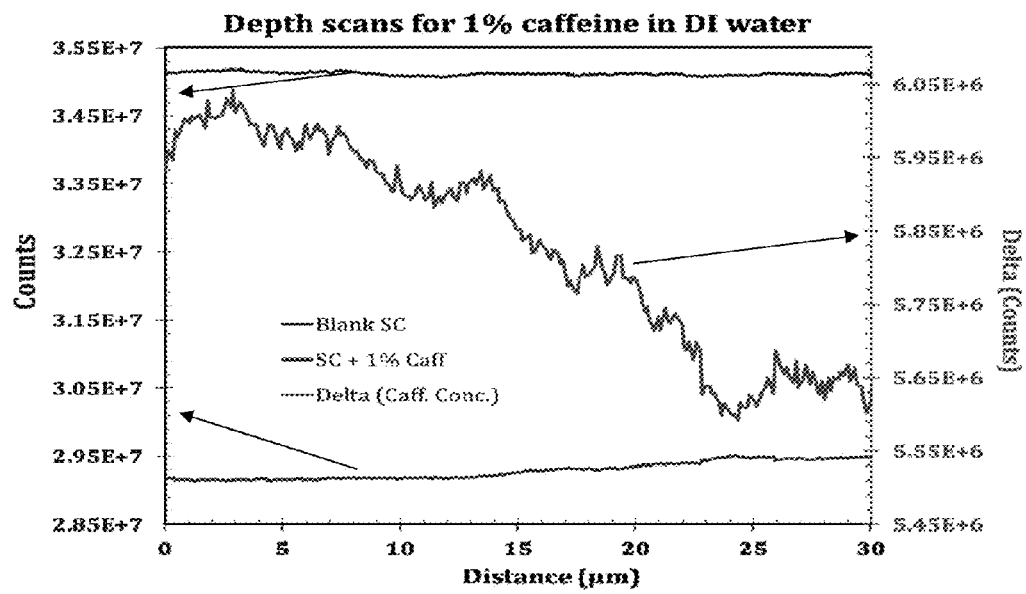
FIG. 31 shows concentration of caffeine solution (right y-axis) in stratum corneum.

Measurements of kinetics and depth scan for blank SC, DI water, and 1% caffeine in DI water were carried out in sequence a similar fashion as described above. Kinetics of DI water and 1% caffeine in DI water are shown in FIG. 30 while FIG. 31 exhibits the concentration profile of caffeine in SC.

Figure 32:
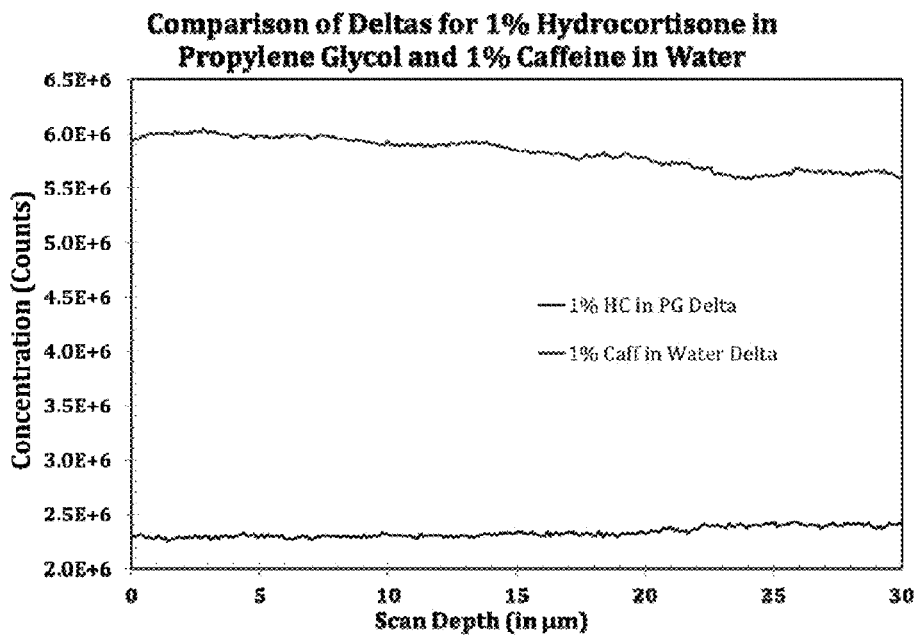
FIG. 32 shows comparison of the concentration profile of hydrocortisone and caffeine solution in the stratum corneum.

FIG. 32 compares the concentration profile of both hydrocortisone and caffeine solution in the SC. It can be seen that there are significantly more hydrocortisone in PG permeated through the SC than caffeine. This is expected and consistent with many observations from front-cell analysis experiments via HPLC. As seen from FIG. 32 and also from FIG. 29, the hydrocortisone profile shows that as we go deeper in the SC, the concentration of hydrocortisone is slightly increased while the caffeine concentration profile (shown in FIG. 31) shows that less caffeine has penetrated deeper in the SC. This observation will be examined further by repeating the measurements and/or by utilizing other solvents.

Figure 33:
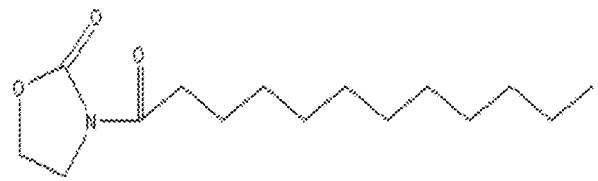
FIG. 33 shows molecular structure of the N-0915.
Figure 34:
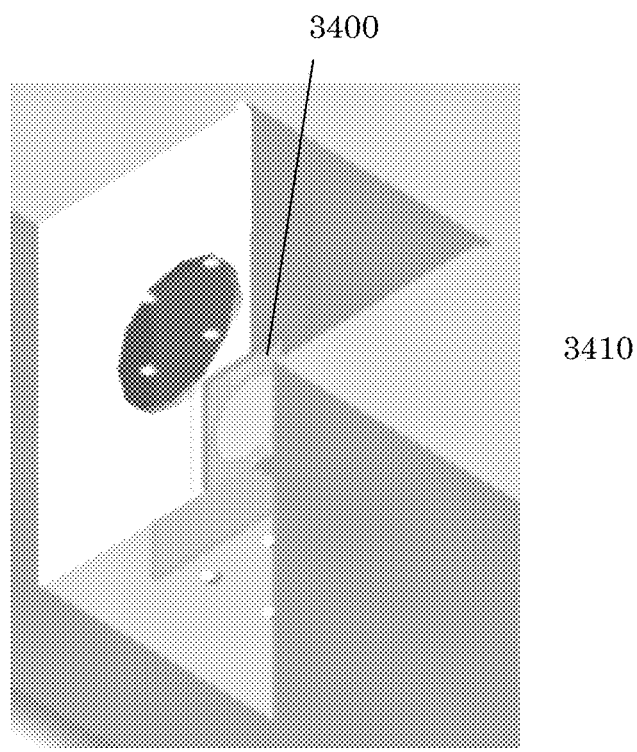
FIG. 34 shows a specimen (stratum corneum) mounted on the spectrometer.

FIG. 34 shows an experimental arrangement where the stratum corneum 3400 is mounted in a terahertz spectrometer 3410 (TeraSpectra, Applied Research & Photonics, Harrisburg, Pa.). A blank specimen was measured first and then another specimen was measured that was saturated with 10 mM N-0915 solution. FIG. 33 shows a molecular structure of the N-0915. Here the objective was to identify the signals obtained in the spectrum to determine whether they attribute to the treatment with specific penetration modifier (N-0915) or to the components of the stratum corneum.

Figure 35:
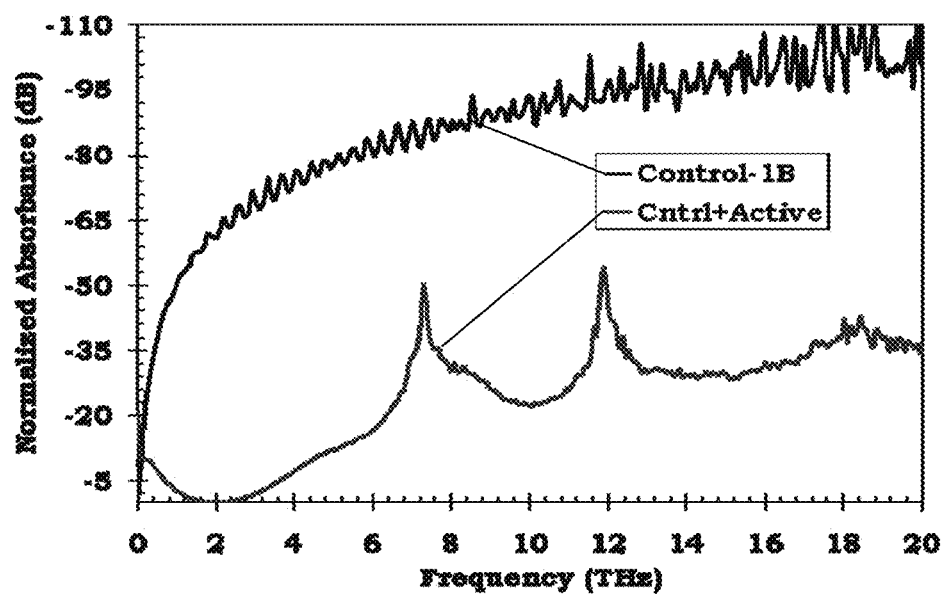
FIG. 35 shows a spectral signature of stratum corneum (control, upper line) and the SC treated with N-0915 (lower line).

FIG. 35 shows the Fourier transform frequency-domain spectra of both blank and N-0915 treated specimen. The spectra are distinctly different in that the SC treated with N-0915 showed prominent peaks in the 7.27 THz, 11.88 THz and 18.42 THz region whereas the control (untreated SC) showed a monotonous increase in absorbance as a function of frequency. While the significance of the peaks in the N-0915 treated specimen need to be explained, it is clear that if the spectra did not cover an extended window (up to 20 THz), then the peaks would not have been visible.

The terahertz scanning reflectometer is an effective tool for quantitative measurement of permeation kinetics and concentration profile of analytes in skin. This method is non-invasive quantitation of analytes in skin. This method can be extended to other tissues or substrates as well as to a variety of analytes. Unlike other methods, this is a simpler technique allowing direct quantification in a noninvasive fashion. These findings are important for quantifying transdermal drug delivery formulation with these solvents and can be extended to other analytes and solvents. Additionally, a wide broadband terahertz spectrometry allows spectroscopic inspection of differences between blank skin (substrate) and those treated with active ingredients. The methods outlined here can be extended to other active/substrate combinations. The N-0915 treated specimen exhibits prominent absorption peaks in the 7.27 THz, 11.88 THz and 18.42 THz region while the spectrum of blank specimen exhibits a monotonous increase of absorbance with frequency. This indicates the importance of broadband terahertz spectroscopy over a wide range (20 THz or more) to be able to probe molecular events.

In general, a terahertz scanning reflectometer for direct measurement of diffusion kinetics and concentration gradient of a substrate includes a platform configured to hold the substratem, and a continuous wave terahertz source configured to generate terahertz radiation. An off-axis parabolic reflector configured to focus the terahertz radiation at a surface of the substrate and a beam splitter configured to direct a reflected beam from the substrate to a detection system. A motion controller configured to move the platform, where on a condition that the motion controller adjusts a location of a focal point inside the substrate, a reflectance measurement is performed across a thickness of the substrate, where a concentration gradient is determined from a blank substrate measurement and a substance loaded substrate measurement, and where on a condition that the motion controller locks the focal point at the surface of the substrate, a real time reflectance measurement is performable upon placement of the substance on the substrate. The substrate may be stratum corneum, and the substance may be an analyte or a solvent. The substance may be selected from the group of permeation enhancers and retardants. The terahertz source and the detection system are an integrated system.

A terahertz dynamic reflectometer for high speed kinetics measurements of a target includes a continuous wave terahertz source configured to generate terahertz radiation toward the target and a detection system for measuring a transient reflective beam from the target upon impact by a ballistic, where the terahertz source and the detection system are angularly positioned outside of a ballistic trajectory. The measured transient may correspond to deformation characteristics. A measured terahertz kinetics spectrum quantifies delamination of different layers within the target. A mass change is determinable from calibrated measurements versus a ballistic impacted target.

The detection system may include a reflective detection system and a transmission detection system. The transmission detection system measures mass change. A velocity profile is determined from a reflected kinetic spectrum and an effective mass of trauma generating volume is obtained from a transmission kinetic spectrum.

A terahertz scanning reflectometer for diagnosing a disease condition of a sample includes a platform configured to hold the sample and a continuous wave terahertz source configured to generate terahertz radiation. An off-axis parabolic reflector configured to focus the terahertz radiation at a surface of the sample and a beam splitter configured to direct a reflected beam from the sample to a detection system. A motion controller configured to move the platform.

On a condition that the motion controller adjusts a location of a focal point inside the sample, a reflectance measurement is performed across a thickness of the sample, where a spectrum is generated at the focal point and compared against a healthy sample to diagnose the disease condition. The spectrum is used to generate a sample image at the focal point. The focal point is moved in multiple dimensions to generate at least one of surface or internal sample images. The spectrum may be sent to an imager system to generate the images using standard techniques.

It is to be understood that the figures and descriptions of embodiments of the folded tape package have been simplified to illustrate elements that are relevant for a clear understanding, while eliminating, for the purpose of clarity, many other elements found in typical electronics packaging. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

Other embodiments of the invention will be apparent to those skilled in the art from a consideration of this specification or practice of the invention disclosed herein; the scope and spirit of the invention being indicated by the following claims.

What is claimed is:

1. A terahertz scanning reflectometer for direct measurement of diffusion kinetics and concentration gradient of a substrate, comprising:
   a platform configured to hold the substrate;
   a continuous wave terahertz source configured to generate terahertz radiation;
   an off-axis parabolic reflector configured to focus the terahertz radiation at a surface of the substrate;
   a beam splitter configured to direct a reflected beam from the substrate to a detection system; and
   a motion controller configured to move the platform,
   wherein on a condition that the motion controller adjusts a location of a focal point inside the substrate, a reflectance measurement is performed across a thickness of the substrate, wherein a concentration gradient is determined from a blank substrate measurement and a substance loaded substrate measurement, and
   wherein on a condition that the motion controller locks the focal point at the surface of the substrate, a real time reflectance measurement is performable upon placement of the substance on the substrate.

2. The terahertz scanning reflectometer of claim 1, wherein the substrate is stratum corneum.

3. The terahertz scanning reflectometer of claim 1, wherein the substance is an analyte.

4. The terahertz scanning reflectometer of claim 1, wherein the substance is a solvent.

5. The terahertz scanning reflectometer of claim 1, wherein the substance is selected from the group of permeation enhancers and retardants.

6. The terahertz scanning reflectometer of claim 1, wherein the terahertz source and the detection system are an integrated system.

7. A terahertz dynamic reflectometer for high speed kinetics measurements of a target, comprising:
   a continuous wave terahertz source configured to generate terahertz radiation toward the target; and
   a detection system for measuring a transient reflective beam from the target upon impact by a ballistic, wherein the terahertz source and the detection system are angularly positioned outside of a ballistic trajectory.

8. The terahertz dynamic reflectometer of claim 7, wherein the transient corresponds to deformation characteristics.

9. The terahertz dynamic reflectometer of claim 7, wherein a terahertz kinetics spectrum quantifies delamination of different layers within the target.

10. The terahertz dynamic reflectometer of claim 7, wherein mass change is determinable from calibrated measurements versus a ballistic impacted target.

11. The terahertz dynamic reflectometer of claim 7, wherein the detection system includes a reflective detection system and a transmission detection system.

12. The terahertz dynamic reflectometer of claim 11, wherein a velocity profile is determined from a reflected kinetic spectrum and an effective mass of trauma generating volume is obtained from a transmission kinetic spectrum.

13. The terahertz dynamic reflectometer of claim 7, wherein the direct detection system measures mass change.

14. A terahertz scanning reflectometer for diagnosing a disease condition of a sample, comprising:
   a platform configured to hold the sample;
   a continuous wave terahertz source configured to generate terahertz radiation;
   an off-axis parabolic reflector configured to focus the terahertz radiation at a surface of the sample;
   a beam splitter configured to direct a reflected beam from the sample to a detection system; and
   a motion controller configured to move the platform,
   wherein on a condition that the motion controller adjusts a location of a focal point inside the sample, a reflectance measurement is performed across a thickness of the sample, wherein a spectrum is generated at the focal point and compared against a healthy sample to diagnose the disease condition.

15. The terahertz scanning reflectometer of claim 14, wherein the spectrum is used to generate a sample image at the focal point.

16. The terahertz scanning reflectometer of claim 14, wherein the focal point is moved in multiple dimensions to generate at least one of surface or internal sample images.

\* \* \* \* \*